(12) United States Patent
Ding et al.

(10) Patent No.: US 11,643,439 B2
(45) Date of Patent: May 9, 2023

(54) MULTI-TARGET COMPOUND WITH ANTICOAGULATION AND ANTIPLATELET ACTIVITY, PREPARATION METHOD THEREFOR, AND USE THEREOF

(71) Applicant: SHAANXI MICOT TECHNOLOGY LIMITED COMPANY, Shaanxi (CN)

(72) Inventors: Wei Ding, Shaanxi (CN); Qiangwei Fan, Shaanxi (CN); Bo Yin, Shaanxi (CN); Guoqin Fu, Shaanxi (CN)

(73) Assignee: SHAANXI MICOT TECHNOLOGY LIMITED COMPANY, Shaanxi (CN)

( * ) Notice: Subject to any disclaimer, the term of this patent is extended or adjusted under 35 U.S.C. 154(b) by 814 days.

(21) Appl. No.: 15/749,622

(22) PCT Filed: Aug. 5, 2015

(86) PCT No.: PCT/CN2015/086173
§ 371 (c)(1),
(2) Date: Feb. 1, 2018

(87) PCT Pub. No.: WO2017/020282
PCT Pub. Date: Feb. 9, 2017

(65) Prior Publication Data
US 2018/0305409 A1    Oct. 25, 2018

(51) Int. Cl.
*C07K 14/00* (2006.01)
*A61K 38/16* (2006.01)
*C07K 9/00* (2006.01)
*A61P 7/02* (2006.01)

(52) U.S. Cl.
CPC ............ *C07K 14/001* (2013.01); *A61K 38/16* (2013.01); *A61P 7/02* (2018.01); *C07K 9/00* (2013.01)

(58) Field of Classification Search
None
See application file for complete search history.

(56) References Cited

U.S. PATENT DOCUMENTS

| | | | |
|---|---|---|---|
| 7,713,928 B1 | 5/2010 | Palepu et al. | |
| 2007/0253966 A1 | 11/2007 | Glaesner et al. | |
| 2016/0083446 A1 | 3/2016 | Erickson | |

FOREIGN PATENT DOCUMENTS

| | | | |
|---|---|---|---|
| CN | 1649625 | 8/2005 | |
| CN | 101284877 A | 10/2008 | |
| JP | 2007505643 A | 3/2007 | |
| JP | 2014502252 A | 1/2014 | |
| WO | WO9015620 A1 | 12/1990 | |
| WO | WO 91/02750 A1 * | 3/1991 | ............... C07K 7/10 |
| WO | WO9102750 A1 | 3/1991 | |
| WO | WO9207874 A1 | 5/1992 | |
| WO | WO 2003/074551 | 9/2003 | |
| WO | WO03090733 A1 | 11/2003 | |
| WO | WO2006102069 A2 | 9/2006 | |

OTHER PUBLICATIONS

Search Report and dated Nov. 28, 2018 from corresponding European Patent Application No. 15900056.1.
International Search Report and Written Opinion dated May 11, 2016 from International Patent Application No. PCT/CN2015/086173 (with English translation of International Search Report).
Gao et al., "Advances in clinical research on glycoprotein IIB/IIIa inhibitors in treatment of acute myocardial infarction," *Pharm. Care Res.*, 13(4):249-252, 2013. (English abstract of Chinese publication).
English translation of Office Communication issued in Chinese Patent Application No. 201580082185.8, dated Nov. 9, 2020.
Office Action dated Jan. 16, 2019 in Japanese Patent Application No. 2018-526284, with English translation.

* cited by examiner

*Primary Examiner* — Sudhakar Katakam
*Assistant Examiner* — Zachary J Miknis
(74) *Attorney, Agent, or Firm* — Parker Highlander PLLC

(57) ABSTRACT

Provided is a multi-target compound with anticoagulation and platelet GPIIb/IIIa receptor antagonism. The formula of the multi-target compound is as follows: A-L-B-L'-C. A and B are binding sites with a thrombin, C is a binding site with a platelet GPIIb/IIIa receptor, L is a first linking group, and L' is a second linking group. Also provided are a preparation method for the compound and use of the compound. The compound has the effects on inhibiting human thrombin activity and a platelet GPIIb/IIIa receptor in vitro, and has the effects on antiplatelet aggregation in vitro/in vivo, and anticoagulation and antithrombosis in vivo.

13 Claims, 9 Drawing Sheets
Specification includes a Sequence Listing.

MULTI-TARGET COMPOUND WITH ANTICOAGULATION AND ANTIPLATELET ACTIVITY, PREPARATION METHOD THEREFOR, AND USE THEREOF

FIELD

The present invention relates to the biomedical field, in particular to a multi-target compound with anticoagulation and platelet GPIIb/IIIa receptor antagonism as well as a preparation method thereof and use thereof.

BACKGROUND

The Sequence Listing associated with this application is hereby incorporated by reference as found in ASCII text file named OP0018_01_0018_20200222_revised_sequence_listing.txt created on Feb. 24, 2020 and having a size in bytes of 12,288.

Thrombosis is an early event during the occurrence of thrombotic diseases and runs through the development of the diseases. Platelet activation and activation of the blood coagulation system play an important role in the process of thrombosis, and are closely related to each other in vivo. Thrombin, which is produced when the blood coagulation system is activated, is a potent platelet activating factor to activate platelets, which in turn facilitates the blood coagulation process. The principle of the prevention and treatment of the thrombotic diseases is to improve the hypercoagulable state, to prevent thrombus extension and new thrombus formation, to dissolve thrombus and then to clear or rebuild the blood flow path, thereby preventing ischemia and necrosis of tissues. Methods for treating the thrombotic diseases include antithrombotic, thrombolytic, interventional and surgical therapies. Among them, the antithrombotic therapy includes antiplatelet and anticoagulant therapies, and it has been of concern as a foundation for the treatment of thrombotic diseases, especially cardiovascular diseases. Anticoagulant drugs prevent the blood coagulation process and thereby prevent thrombosis by acting on blood coagulation factors; antiplatelet drugs inhibit thrombosis by functions of inhibiting platelet adhesion, aggregation and release. Currently, clinically used thrombin inhibitors mainly include low molecular weight heparin and bivalirudin; and platelet GPIIb/IIIa receptor antagonists mainly include lamivudine, tirofiban, etc. These drugs have side effects such as bleeding tendency, and are subjected to some application limitations. More importantly, all of these drugs inhibit thrombosis through a single target site, and currently, drugs for different target sites are often used in combination clinically, so as to achieve clinical effects in terms of increase in efficacy and reduction of side effects. However, currently, for the drug combination, there are problems, such as dose matching, bleeding, coordination, which has great influences on the clinical antithrombotic effect.

Therefore, it is necessary to develop a technical solution which is capable of inhibiting thrombosis by multi-target inhibition, so as to achieve the effect of simultaneous action on different target sites by administration of a single drug and to avoid the problems caused by the drug combination.

SUMMARY

An object of the present invention is to overcome the defects existing in the prior art and to provide a multi-target antagonistic compound which is capable of simultaneously targeting thrombin and platelet GPIIb/IIIa receptors.

The present disclosure provides a multi-target antagonistic compound with anticoagulation and platelet GPIIb/IIIa receptor antagonism, said compound having a structure represented by Formula (1): A-L-B-L'-C Formula (1), wherein A and B are thrombin binding sites, C is a platelet GPIIb/IIIa receptor binding site, L is a first linker, and L' is a second linker.

Optionally, L' has a structure represented by Formula (2):

$$((Gly)_{n1}\text{-}(Ser)_{n2})_{n3}, \quad \text{Formula(2)},$$

wherein n1 is 1, 2, 3 or 4: n2 is 0 or 1; and n3 is 0, 1, 2 or 3, sequences of which are further set forth in SEQ ID No. 8 to SEQ ID No. 14.

Optionally, L' has a structure represented by Formula (3):

$$(\text{Glu-Ala-Ala-Ala-Lys})n_1 \quad \text{Formula (3)},$$

wherein n1 is 0,1, 2 or 3, sequences of which are further set forth in SEQ ID No. 15 to SEQ ID No. 17.

Optionally, L' has a structure represented by Formula (4):

$$(\text{Arg-Val-Leu-Ala-Glu-Ala})n_1 \quad \text{Formula (4)},$$

wherein n1 is 0, 1, 2 or 3, sequences of which are further set forth in SEQ ID No. 18 to SEQ ID No. 20.

Optionally, A has a structure represented by Formula (5):

$$A1\text{-}A2\text{-}A3\text{-}A4 \quad \text{Formula (5)},$$

wherein A1 is D-Phe; A2 is Pro or Pip; A3 is Arg, Lys, Orn or Har; and A4 is Pro, D-Pro or Ser.

Optionally, B has a structure represented by Formula (6):

$$B1\text{-}B2\text{-}B3\text{-}B4\text{-}B5 \quad \text{Formula (6)},$$

wherein B1 is a dipeptide consisting of any two acidic amino acids; B2 is Val, Leu, Ile, Nle or Phe; B3 is Hyp, Ser, Pro or an N-methyl amino acid; B4 is a dipeptide consisting of any two acidic amino acids; B5 is an amino acid selected from the group consisting of Tyr, Trp, Phe, Leu, Nle, Ile, Val, Cha and Pro, or B5 is a dipeptide comprising at least one amino acid selected from Tyr, Trp, Phe, Leu, Nle, He, Val, Cha and Pro.

Optionally, C has a structure represented by Formula (7):

$$\text{Cys-Har-C1-Asp-Trp-Pro-C2} \quad \text{Formula(7)},$$

wherein C1 is Gly or Ser; C2 is Cys or a structure obtained by replacing —OH in Cys with —NH$_2$; and a disulfide bond is formed between two mercapto groups in the Formula (7), sequences of which are further set forth in SEQ ID No. 21 to SEQ ID No. 22.

Optionally, L has a structure represented by Formula (8):

$$\text{L1-L2-L3-L4-Gly-Asp-L5} \quad \text{Formula (8)},$$

wherein L1 is Gly, Ala, Val or Gly-Gly; L2 is Gly or Cys; L3 is Gly, Gly-Gly, Gly-Gly-Gly or a dextrorotatory amino acid; L4 is Asn or Gln; L5 is one selected from Phe, Tyr, a derivative in which a benzene ring of Phe is substituted, and a derivative in which a benzene ring of Tyr is substituted.

Optionally, A-L-B is selected from one of the polypeptide sequences shown in SEQ ID No. 1 to SEQ ID No. 3.

Optionally, said compound has a structure represented by Formula (9):

$$X\text{-}A\text{-}L\text{-}B\text{-}L'\text{-}C\text{—}Y \quad \text{Formula (9)},$$

wherein X is one selected from hydrogen, one or two C1-C6 alkyl, one or two C2-C10 acyl, benzyloxycarbonyl and tert-butoxycarbonyl; Y is one selected from OH, C1-C6 alkoxy, an amino, and an amino substituted with one or two C1-C4 alkyl.

Optionally, said compound comprises a polypeptide sequence of polypeptide structures shown in SEQ ID No.4 to SEQ ID No.7.

Optionally, said compound is selected from one of polypeptide structures shown in SEQ ID No.4 to SEQ ID No.7.

The present disclosure further provides a salt of the multi-target antagonistic compound with anticoagulation and platelet GPIIb/IIIa receptor antagonism.

Optionally, said salt is an acetate salt of the compound or a trifluoroacetate salt of the compound.

The present disclosure further provides a method for preparing the compound of the present disclosure, wherein the method comprises the steps of:

(1) sequentially connecting protected amino acids or fragments starting from a carboxyl terminal according to a polypeptide sequence using a solid phase synthesis method, to obtain a polypeptide-Wang resin in which side chains of amino acids are all protected; (2) subjecting the polypeptide-Wang resin in which side chains of amino acids are all protected to acid hydrolysis with an acid hydrolyzing agent to obtain a crude linear polypeptide; and (3) cyclizing the crude linear polypeptide to form a disulfide bond and then purifying the resultant with high-pressure preparative liquid chromatography, to obtain a polypeptide sequence.

The present disclosure also provides a pharmaceutical composition, wherein said pharmaceutical composition comprises the compound of the present disclosure or a salt of the compound of the present disclosure as an active ingredient.

Optionally, the dosage form of said pharmaceutical composition is an injection, a tablet, a capsule, a pill, a powder, a granule, a suspension or an emulsion.

The present disclosure also provides use of the compound of the present disclosure or a salt of the compound of the present disclosure in the manufacture of a medicament for the prevention and treatment of peripheral arterial thrombosis, arterial and venous bypass thrombosis. The present disclosure also provides use of the compound of the present disclosure or a salt of the compound of the present disclosure in the manufacture of a medicament for the prevention and treatment of progressive ischemic stroke, in the manufacture of a medicament for the treatment of thrombosis in acute coronary syndromes, percutaneous coronary intervention, or therapy with a coronary stent in PCI, in the manufacture of a medicament for the prevention and treatment of acute pulmonary embolism, or in the manufacture of a medicament for the prevention and treatment of thrombosis in organ and tissue transplantation.

The multi-target antagonistic compound with anticoagulation and platelet GPIIb/IIIa receptor antagonism provided in the present disclosure has a direct, reversible and specific anti-thrombin function and also inhibits the GPIIb/IIIa receptors, which can achieve the anticoagulant and anti-thrombotic effect at a low dose. At the same time, the bleeding risk is reduced, and problems such as dose matching, bleeding, coordination and the like caused by drug combination are avoided.

DETAILED DESCRIPTION OF EMBODIMENTS

Figure 1:
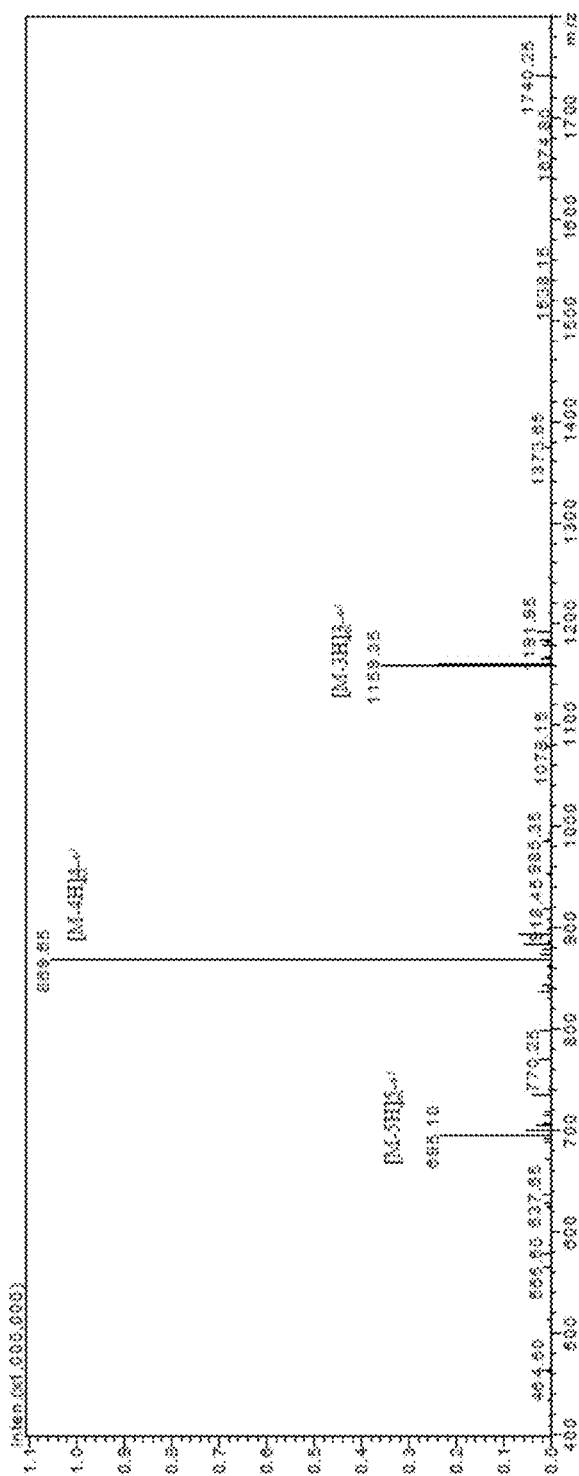
FIG. 1 shows detection results of mass spectrometry of polypeptide 1.

The present disclosure will be described in detail by way of specific embodiments hereinafter. It should be understood that the following embodiments are given for an illustrative purpose only and are not intended to limit the scope of the present disclosure. Those skilled in the art can make various modifications and replacements to the present disclosure without departing from the spirit and scope of the present disclosure.

In the present disclosure, the thrombin refers to a proteolytic enzyme formed from a thrombin precursor (an essential component in blood plasma) that can promote blood coagulation by catalyzing the conversion of fibrinogen to fibrin. Platelet GPIIb/IIIa receptor is an adhesive glycoprotein on the surface of platelets, which is a member of integrin families. Each inactivated platelet has approximately 50,000 to 80,000 GPIIb/IIIa receptor molecules on its surface and is the most abundant integrin on the platelet surface. Amino acid refer to a general term for a class of organic compounds containing amino and carboxyl groups, which is a basic constituent unit of a protein and is a basic substance of proteins required for animal nutrition. The amino acids in the present disclosure are expressed by their conventional abbreviations in the art. Acidic amino acid refers to an amino acid having an isoelectric point of less than 7, including aspartic acid (Asp) and glutamic acid (Glu). The N-methyl amino acid refers to an amino acid obtained by substitution of an amino in the amino acids with a methyl. A derivative in which a benzene ring is substituted means a derivative of an amino acid in which a benzene ring of the amino acid is substituted with a linear or branched alkyl, a halogen, an alkoxy, an amide, an acyloxy or the like. A C1-C6 alkyl means an alkyl having 1 to 6 carbon atoms, and a C2-C10 acyl means an acyl having 2 to 10 carbon atoms.

An embodiment of the present disclosure provides a multi-target antagonistic compound with anticoagulation and platelet GPIIb/IIIa receptor antagonism, said compound having a structure represented by Formula (1): A-L-B-L'-C Formula (1), wherein A and B are thrombin binding sites. C is a platelet GPIIb/IIIa receptor binding site, L is a first linker, and L' is a second linker. Herein, the first linker L' connects A and B together to form a A-L-B structure, and the second linker L' connects the A-L-B structure and a C structure together to form the structure represented by Formula (1). In an embodiment of the present disclosure, the A-L-B structure can be directly connected to the C structure to form a multi-target antagonistic compound.

In an embodiment of the present disclosure, L' may be a structure represented by Formula (2):

$$((Gly)_{n1}\text{-}(Ser)_{n2})_{n3},\qquad\text{Formula (2).}$$

In the formula (2), n1 is 1, 2, 3 or 4; n2 or 1; and n3 is 0, 1, 2 or 3. Sequences of this embodiment are further set forth in SEQ ID No. 8 to SEQ ID No. 14.

In a preferred embodiment, L' has a structure of Gly-Gly-Gly-Gly-Ser or Gly-Gly-Gly-Ser.

In an embodiment of the present disclosure, L' may be a structure represented by Formula (3):

$$(\text{Glu-Ala-Ala-Ala-Lys})_{n1}\qquad\text{Formula (3),}$$

wherein n1 is 0, 1, 2, or 3. Sequences of this embodiment are further set forth in SEQ ID No. 15 to SEQ ID No. 17.

In a preferred embodiment, L' has a structure of Glu-Ala-Ala-Ala-Lys (see SEQ ID No. 15).

In an embodiment of the present disclosure, L' may be a structure represented by Formula (4):

$$(\text{Arg-Val-Leu-Ala-Glu-Ala})_{n1}\qquad\text{Formula (4),}$$

wherein n1 is 0, 1, 2 or 3, sequences of this embodiment are further set forth in SEQ ID No. 18 to SEQ ID No. 20.

In a preferred embodiment, L' has a structure of Arg-Val-Leu-Ala-Glu-Ala.

In an embodiment of the present disclosure, A has a structure represented by Formula (5): A1-A2-A3-A4 Formula (5), wherein A1 is D-Phe; A2 is Pro or Pip; A3 is Arg, Lys, Orn or Har; and A4 is Pro, D-Pro or Ser. Herein, Pip refers to 4-aminopiperidinyl-4-carboxy, Orn refers to ornithine, and Har refers to homoarginine.

In a preferred embodiment, A has a structure of D-Phe-Pro-Arg-Pro.

In an embodiment of the present disclosure, B has a structure represented by Formula (6):

$$\text{B1-B2-B3-B4-B5}\qquad\text{Formula (6),}$$

wherein B1 is a dipeptide consisting of any two acidic amino acids; B2 is Val, Leu, Ile, Nle or Phe; B3 is Hyp, Ser, Pro or an N-methyl amino acid; B4 is a dipeptide consisting of any two acidic amino acids; B5 is an amino acid selected from the group consisting of Tyr, Trp, Phe, Leu, Nle, Ile, Val, Cha and Pro, or B5 is a dipeptide comprising at least one amino acid selected from Tyr, Trp, Phe, Leu, Nle, Ile, Val, Cha and Pro. Herein, Nle represents norleucine, and Hyp represents hydroxyproline. This embodiment is further set forth in set forth in SEQ ID No. 26.

In a preferred embodiment, B has a structure of Glu-Glu-Ile-Pro-Glu-Glu-Tyr-Leu (see SEQ ID No. 23).

Optionally, C has a structure represented by Formula (7):

$$\text{Cys-Bar-C1-Asp-Trp-Pro-C2}\qquad\text{Formula (7),}$$

wherein C1 is Gly or Ser; C2 is Cys or a structure obtained by replacing —OH in Cys with —NH$_2$; and a disulfide bond is formed between two mercapto groups in the Formula (7).

Herein, Har represents homoarginine. Sequences of these embodiments are further set forth in SEQ ID No. 21 to SEQ ID No. 22.

Optionally, L has a structure represented by Formula (8): L1-L2-L3-L4-Gly-Asp-L5 Formula (8), wherein L1 is Gly. Ala. Val or Gly-Gly; L2 is Gly or Cys; L3 is Gly, Gly-Gly. Gly-Gly-Gly or a dextrorotatory amino acid; L4 is Asn or Gln; L5 is selected from one of Phe, Tyr, a derivative in which a benzene ring of Phe is substituted, and a derivative in which a benzene ring of Tyr is substituted. Herein L1 is preferably Gly-Gly, L2 is preferably Gly, L3 is preferably Gly, L4 is preferably Asn, and L5 is preferably Phe.

In a preferred case, A-L-B is selected from one of sequences shown in SEQ ID No. 1 to SEQ ID No. 3. In the sequences shown in SEQ ID No. 1 to SEQ ID No. 3, phenylalanine at the N-terminal is D-phenylalanine.

SEQ ID No. 1:
D-Phe Pro Arg Pro Gly Gly Gly Gly Asn Gly Asp Tyr
Glu Asp Ile Pro- Glu Glu Tyr Leu

SEQ ID No. 2:
D-Phe Pro Arg Ser Gly Gly Gly Gly Asn Gly Asp Phe
Glu Asp Ile Pro Glu Glu Tyr Leu

SEQ ID No. 3:
D-Phe Pro Arg Pro Gly Gly Gly Gly Asn Gly Asp Phe
Glu Glu Ile Pro- Glu Glu Tyr Leu

In an embodiment of the present disclosure, said compound has a structure represented by Formula (9):

$$\text{X-A-L-B-L'-C—Y}\qquad\text{Formula (9),}$$

wherein X is selected from one of hydrogen, one or two C1-C6 alkyl groups, one or two C2-C10 acyl groups, benzyloxycarbonyl or tert-butoxycarbonyl, in which optionally, the C1-C6 alkyl group may be methyl or ethyl; Y is selected from one of OH, C1-C6 alkoxy, amino, amino substituted by one or two C1-C4 alkyl, in which in an embodiment of the present disclosure, Y is OH or NH$_2$. In a particularly preferred embodiment, when the compound has the structure shown in SEQ ID No. 5 and Y at the C-terminal is NH$_2$, the compound binds to the platelet GPIIb/IIIa receptor for a longer time and has a better platelet inhibitory function.

Herein, the alkyl group may be a linear structure or a branched structure, and the acyl group may be a linear structure or a branched structure, wherein when X is two C1-C6 alkyl groups, the kinds of the two C1-C6 alkyl groups may be the same or different; wherein when X is two C2-C10 acyl groups, the kinds of the two C2-C10 acyl groups may be the same or different. When Y is an amino substituted by two C1-C4 alkyls, the kinds of the C1-C4 alkyl-substituted amino groups may be the same or different.

Optionally, the compound comprises a polypeptide sequence of polypeptide structures shown in SEQ ID No.4 to SEQ ID No.7. In the polypeptide sequences shown in SEQ ID No. 4 to SEQ ID No. 7, phenylalanine at the N-terminal is D-phenylalanine.

SEQ ID No. 4:
D-Phe Pro Arg Pro Gly Gly Gly Gly Asn Gly Asp Phe
Glu Glu Ile Pro Glu Glu Tyr Leu Gly Gly Gly Gly
Ser Cys Har Gly Asp Trp Pro Cys

-continued

```
SEQ ID No. 5:
D-Phe Pro Arg Pro Gly Gly Gly Gly Asn Gly Asp Phe
Glu Glu Ile Pro Glu Glu Tyr Leu Glu Ala Ala Ala
Lys Cys Har Gly Asp Trp Pro Cys

SEQ ID No. 6:
D-Phe Pro Arg Pro Gly Gly Gly Gly Asn Gly Asp Phe
Glu Glu Ile Pro Glu Glu Tyr Leu Cys Har Gly Asp
Trp Pro Cys

SEQ ID No. 7:
D-Phe Pro Arg Pro Gly Gly Gly Gly Asn Gly Asp Phe
Glu Glu Ile Pro Glu Glu Tyr Leu Arg Val Leu Ala
Glu Ala Cys Har Gly Asp Trp Pro Cys
```

In a preferred embodiment of the present disclosure, said compound is selected from one of polypeptide structures shown in SEQ ID No.4 to SEQ ID No.7.

In one aspect of the present disclosure, a salt of the multi-target antagonistic compound with anticoagulation and platelet GPIIb/IIIa receptor antagonism is provided.

In the present disclosure, the salt is in a form of a pharmaceutically acceptable salt. The "pharmaceutically acceptable salt" refers to a salt suitable for being contact with human or animal tissues without excessive toxicity, stimulation, allergies, and the like. The pharmaceutically acceptable salt is well known in the art. Such a salt can be prepared in the final separation and purification of the peptide compound of the present disclosure, and also can be separately prepared by reacting a free base or acid with a suitable organic or inorganic acid or base. Representative acid addition salts include, but are not limited to, acetate, trifluoroacetate, dihexanoate, citrate, aspartate, benzoate, benzenesulfonate, bisulfate, butyrate, heptanoate, hexanoate, fumarate, hydrochloride, hydrobromide, hydroiodide, lactate, maleate, mesylate, oxalate, propionate, phosphate, glutamate, bicarbonate, p-toluenesulfonate. Preferably, the salt is an acetate, trifluoroacetate or hydrochloride salt of the compound, and particularly preferably, the salt is an acetate salt or a trifluoroacetate salt of the compound.

In one aspect of the present disclosure, a method for preparing the multi-target antagonistic compound with anticoagulation and platelet GPIIb/IIIa receptor antagonism of the present disclosure is provided, wherein said method comprises the steps of: (1) sequentially connecting protected amino acids or fragments starting from a carboxyl terminal according to a polypeptide sequence using a solid phase synthesis method, to obtain a polypeptide-Wang resin in which side chains of amino acids are all protected; (2) subjecting the polypeptide-Wang resin in which side chains of amino acids are all protected to acid hydrolysis with an acid hydrolyzing agent to obtain a crude linear polypeptide; (3) cyclizing the crude linear polypeptide to form a disulfide bond and then purifying the resultant with high-pressure preparative liquid chromatography, to obtain a polypeptide sequence.

In one aspect of the present disclosure, a pharmaceutical composition is also provided, wherein said pharmaceutical composition comprises a multi-target antagonistic compound with anticoagulation and platelet GPIIb/IIIa receptor antagonism of the present disclosure or a salt of the compound as an active ingredient. Optionally, the pharmaceutical composition further comprises a pharmaceutically acceptable carrier. The pharmaceutical composition may be in a form of an injection or a microemulsion. The pharmaceutically acceptable carriers commonly used in the art can be selected and used according to the form of the pharmaceutical composition. In the pharmaceutical composition, the content of the active ingredient is not less than 85%. The kind of the carrier includes but is not limited to physiological saline. The pharmaceutical composition of the present disclosure can be used for the treatment and/or prevention of thrombotic diseases, and its main functions include anticoagulation, antithrombosis and antiplatelet aggregation. A medicament comprising the multi-target antagonistic compound with anticoagulation and platelet GPIIb/IIIa receptor antagonism or a salt of the compound as an active ingredient is administered to a subject.

In one aspect of the present disclosure, use of a compound of the present disclosure or a salt of the compound of the present disclosure in the manufacture of a medicament for the prevention and treatment of peripheral arterial thrombosis, arterial and venous bypass thrombosis is also provided. In one aspect of the present disclosure, use of a compound of the present disclosure or a salt of the compound of the present disclosure in the manufacture of a medicament for the prevention and treatment of progressive ischemic stroke is also provided. In one aspect of the present disclosure, use of a compound of the present disclosure or a salt of the compound of the present disclosure in the manufacture of a medicament for the prevention and treatment of acute pulmonary embolism is also provided. The present disclosure also provides use of a compound of the present disclosure or a salt of the compound of the present disclosure in the manufacture of a medicament for the prevention and treatment of thrombosis in organ and tissue transplantation, in the manufacture of a medicament for the treatment of acute coronary syndromes, percutaneous coronary intervention, or treatment with a coronary stent placed in PCI, in the manufacture of a medicament for the prevention and treatment of acute pulmonary embolism, and in the manufacture of a medicament for the prevention and treatment of thrombosis in organ and tissue transplantation. The uses described in the present disclosure include the manufacture of a medicament comprising the compound of the present disclosure, and the dosage form of the medicament includes but is not limited to a lyophilized powder for injection, an injection, a microemulsion, a microsphere, a micelle and other dosage forms. The antithrombotic medicament includes medicaments for the treatment or prevention of peripheral arterial occlusive diseases (functioning through anticoagulation, antithrombosis, antiplatelet aggregation), progressive ischemic stroke, acute coronary syndromes and the like. In addition, the antithrombotic medicament may also include medicaments for the prevention of the thrombosis of arteriovenous fistulas in a hemodialysis patient during VAF and VAG surgeries.

Hereinafter, the specific embodiments of the present disclosure will be further described by way of examples. The instruments and reagents involved in the following examples can all be obtained by purchasing commercially available products.

Some experimental materials in the following examples are shown in Table 1, and the instruments are shown in Table 2.

TABLE 1

| Name | Manufacturer | Specification | Lot No. |
|---|---|---|---|
| Sodium citrate | Tianjin Baishi Chemical Co., Ltd. | 500 g/bottle | 20050318 |
| 0.9% NaCl injection | Xi'an Jingxi Shuanghe Pharmaceutical Co., Ltd. | 250 mL/bottle | 11806471 |
| PT Assay Kit | Shaanxi Ark Biotechnology Co., Ltd. | 10 × 2 ml | 20140913 |
| APPT Assay Kit | Shaanxi Ark Biotechnology Co., Ltd. | 10 × 2 ml | 20141012 |

TABLE 2

| Name | Manufacturer | Model |
|---|---|---|
| Electronic balance | Sartorius Scientific Instruments (Beijing) Co., Ltd. | BSA124S-CW |
| Centrifuge | Anhui Zhongke Zhongjia Scientific Instrument Co., Ltd. | SC-3610 |
| Precise microsampler | Nichipet, Japan | 5 μl, 100 μl, 200 μl, 1000 μl |
| Platelet-aggregation coagulation factor analyzer | Beijing Steellex Scientific Instrument Co., Ltd. | LG-PABER-1 |
| Bleeding time tester | Jiangsu Kangjian Medical Apparatus Co., Ltd. | 5 mm wide, 1 mm deep |
| Temperature tester | Home-made | |

Example 1

Example 1 is used to illustrate a compound according to one embodiment of the present disclosure and its preparation process.

1. Preparation of Fragment I: Fmoc-Gly-Gly-Gly-Gly-OH. Sequences related to this embodiment are set forth SEQ ID No. 8 to SEQ ID No. 14.

An Fmoc-Gly-2-C1-Trt-resin (23.5 g, 16.5 mmol) with a degree of substitution of 0.7 mmol/g was subjected to deprotection of Fmoc with 2.5 L of 25% PIP/DMF solution for 25 minutes. The resin was filtered, and then washed by turns with DMF and DCM for three times, with not less than 1 minute each time. Fmoc-Gly-OH (14.8 g, 50 mmol) was added and stirred for reaction for 4 hours at 30° C. The reaction was detected for its end point by a ninhydrin method. After the reaction was completed, the resin was filtered and washed by turns with DMF and DCM for three times.

The above steps were repeated twice to connect two additional Gly residues, finally obtaining an Fmoc-Gly-Gly-Gly-Gly-2-C1-Trt-resin. The resulted resin was dissolved in 5 L of 30% hexafluoroisopropanol/DCM solution and stirred for reaction for 2 hours. The filtrate was collected by filtration and dried under vacuum at 30° C. for 10 hours to give 7.2 g of Fmoc-Gly-Gly-Gly-Gly-OH, with a yield of 96% and a purity of 95.6%, MS m/z: 469 (M+1).

Sequences related to this embodiment are set forth SEQ ID No. 8 to SEQ ID No. 14.

2. Preparation of Fragment II: Fmoc-Cys(Trt)-Har-Gly-Asp(OtBu)-Trp-Pro-Cys(Trt)-Wang Resin (see SEQ ID No. 24).

10 g of the Fmoc-Cys(Trt)-Wang resin (load 1.0 mmol/g, 10 mmol) was weighed and placed in a solid phase reactor, to which 150 mL of 25% PIP/DMF solution was added for deprotection, which was stirred at 25° C. for 30 minutes. After the reaction was completed, the resin was washed by turns with DMF and DCM for three times. Fmoc-Pro-OH (10.1 g, 30 mmol) and HOBt (4.05 g, 30 mmol) were dissolved in 150 ml of DMF and added to the reactor. To the reaction mixture DIC (3.78 g, 30 mmol) was slowly added at 0° C. to 5° C., then the deprotected amino acid resin was added, and stirred for reaction at 30° C. for 3 hours. The reaction was detected for its end point by the ninhydrin method. After the reaction was completed, the resin was filtered, and washed by turns with DMF and DCM for three times. The above steps were repeated, and Fmoc-Trp-OH, Fmoc-Asp(OtBu)-OH, Fmoc-Gly-OH, Fmoc-Har-OH and Fmoc-Cys(Trt)-OH were sequentially coupled in accordance with the peptide sequence, to obtain Fmoc-Cys(Trt)-Har-Gly-Asp(OtBu)-Trp-Pro-Cys(Trt)- Wang resin, of which the degree of substitution was detected to be 0.6 mmol/g. A sequence regarding this embodiment is further set forth in SEQ ID No. 27.

3. Synthesis of Linear Polypeptide 1-Resin

Linear polypeptide 1-resin was Fmoc-D-Phe-Pro-Arg(pbf)-Pro-Gly-Gly-Gly-Gly-Asn(Trt)-Gly-Asp(OtBu)-Ile-Pro-Glu(OtBu)-Glu(OtBu)-Tyr(OtBu)-Leu-Gly-Gly-Gly-Gly-Ser(Trt)-Cys(Trt)-Har-Gly-Asp(OtBu)-Trp-pro-Cys(Trt)-Wang (see SEQ ID No. 24 to see SEQ ID No. 25).

To 20 g of Fmoc-Cys(Trt)-Har-Gly-Asp(OtBu)-Trp-Pro-Cys(Trt)-Wang resin (degree of substitution: 0.6 mmol/g, 12 mmol), 300 ml of 25% PIP/DMF solution was added for deprotection, which was stirred at 25° C. for 30 minutes. After the reaction was completed, the resin was washed by turns with DMF and DCM for three times. Fmoc-Ser(Trt)-OH (20.5 g, 36 mmol) and HOBt (4.86 g, 36 mmol) were dissolved in 150 ml of DMF and added to the reactor. To the reaction mixture DIC (4.53 g, 36 mmol) was slowly added at 0° C. to 5° C., then the deprotected amino acid resin was added, and stirred for reaction at 30° C. for 3 hours. The reaction was detected for its end point by the ninhydrin method. After the reaction was completed, the resin was filtered and washed by turns with DMF and DCM for three times. Fmoc-Gly-Gly-Gly-Gly-OH, Fmoc-Leu-OH, Fmoc-Tyr(OtBu)-OH, Fmoc-Glu(OtBu)-OH, Fmoc-Glu(OtBu)-OH, Fmoc-Pro-OH, Fmoc-Ile-OH, Fmoc-Glu(OtBu)-OH, Fmoc-Glu(OtBu)-OH, Fmoc-Phe-OH, Fmoc-Asp(OtBu)-OH, Fmoc-Gly-OH, Fmoc-Asn(Trt)-OH, Fmoc-Gly-Gly-Gly-Gly-OH, Fmoc-Pro-OH, Fmoc-Arg(pbf)-OH, Fmoc-Pro-OH and Fmoc-D-Phe-OH were sequentially introduced with the above method, to obtain polypeptide 1-Wang resin in which side chains of amino acids are all protected.

Embodiments of the foregoing are additionally set forth in SEQ ID No. 27.

4. Preparation of Crude Linear Polypeptide 1

20 g of the polypeptide 1-Wang resin in which side chains of amino acids are all protected prepared in Step 3 was added to an acidizing agent (trifluoroacetic acid:triisopropylsilane:water=190 ml: 5 ml: 5 ml), and reacted at 25° C. for 2 hours. The resin was filtered, and washed with a small amount of trifluoroacetic acid, and the filtrate was combined.

Under vigorous stirring, the filtrate was slowly added to 1.1 L precooled diethyl ether and a white precipitate appeared. After standing for 1 hour, the mixture was subjected to suction filtration, and the filter cake was washed with ice diethyl ether for 5 times and dried under vacuum to obtain 6 g of crude product.

5. Disulfide Bond Formation and Purification of Polypeptide 1

Polypeptide 1 has a structural formula as shown below (a polypeptide sequence shown in SEQ ID No. 4): D-Phe Pro Arg Pro Gly Gly Gly Gly Asn Gly Asp Phe Glu Glu Ile Pro Glu Glu Tyr Leu Gly Gly Gly Gly Ser Cys Har Gly Asp Trp Pro Cys. 10 g of the linear polypeptide 1 prepared in step 4 was dissolved in 200 ml pure water, and thereto a 5% 12 solution was slowly add dropwise under stirring. The reaction was detected by HPLC. After the reaction was completed, the target product was purified by high performance liquid chromatography and lyophilized to obtain the final product polypeptide 1 in a weight of 1 g. Detection results of mass spectrometry of polypeptide 1 are shown in FIG. 1.

Example 2

Figure 2:
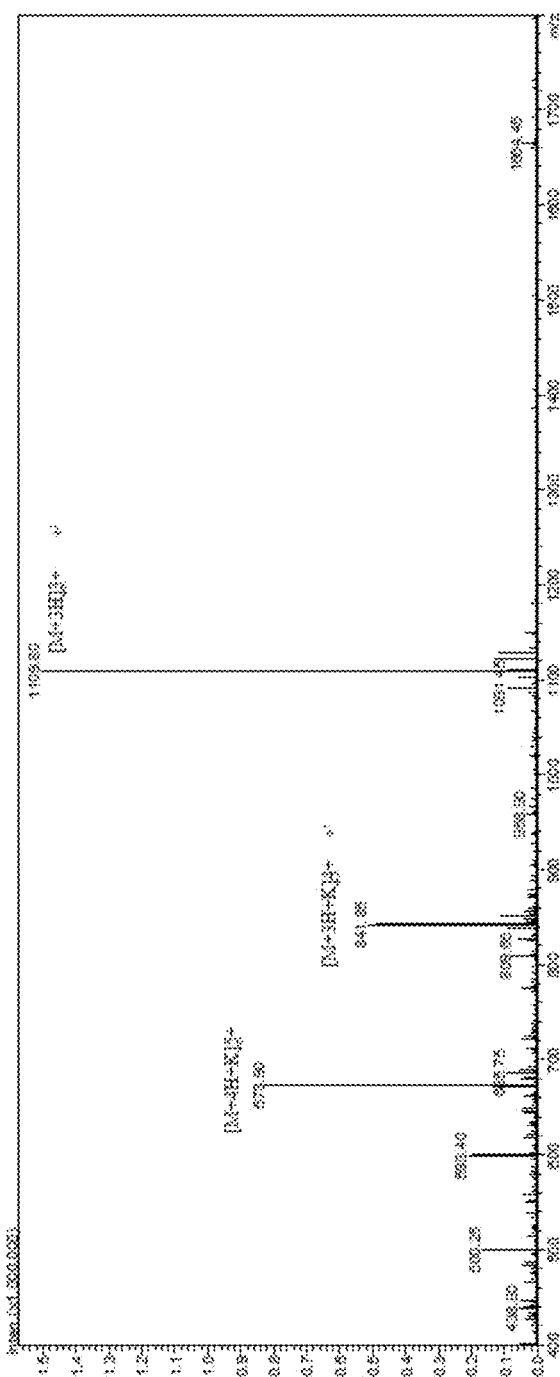
FIG. 2 shows detection results of mass spectrometry of polypeptide 2.

Polypeptide 2 was prepared in the same manner as Example 1, except that the L' fragment was Glu Ala Ala Ala Lys, to obtain polypeptide 2 in a product weight of 1.2 g. Detection results of mass spectrometry of polypeptide 2 are shown in FIG. 2.

Polypeptide 2 has a structural formula as shown below (a polypeptide sequence shown in SEQ ID No. 5): D-Phe Pro Arg Pro Gly Gly Gly Gly Asn Gly Asp Phe Glu Glu Ile Pro Glu Glu Tyr Leu Glu Ala Ala Ala Lys Cys Har Gly Asp Trp Pro Cys Example 3

Figure 3:
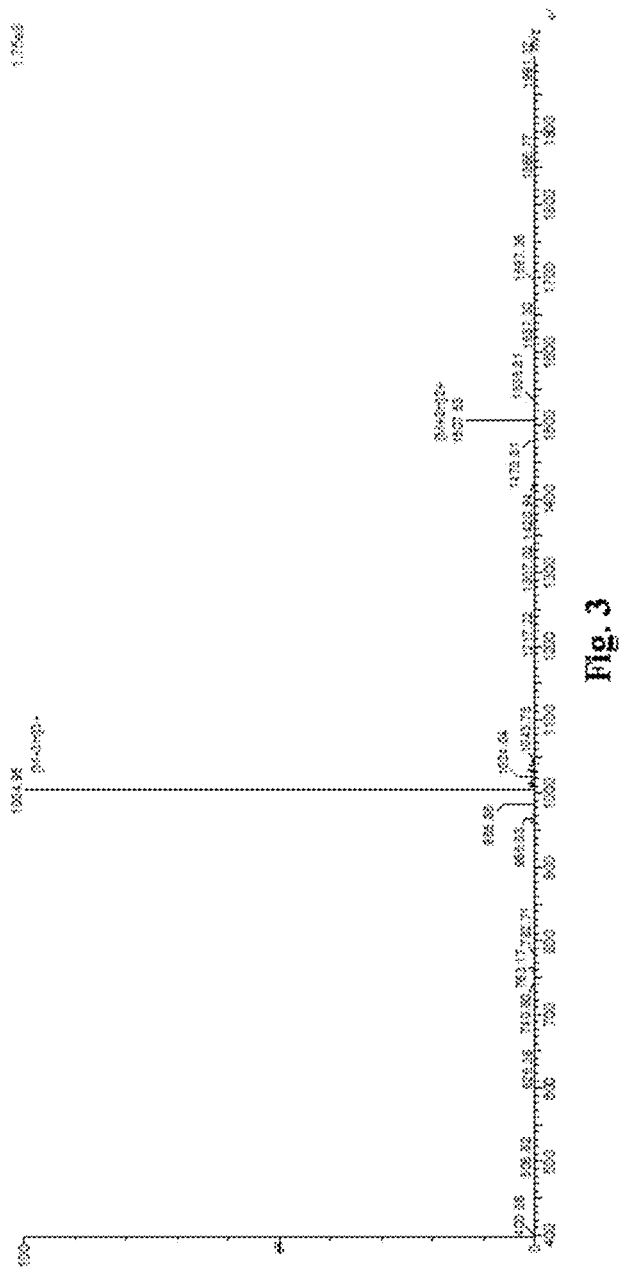
FIG. 3 shows detection results of mass spectrometry of polypeptide 3.

Polypeptide 3 was prepared in the same manner as Example 1, except that the fragment Gly Gly Gly Gly Ser (i.e., the fragment L') was removed to obtain polypeptide 3 in a product weight of 1.5 g. Detection results of mass spectrometry of polypeptide 3 are shown in FIG. 3.

Polypeptide 3 has a structural formula as shown below (a polypeptide sequence shown in SEQ ID No. 6): D-Phe Pro Arg Pro Gly Gly Gly Gly Asn Gly Asp Phe Glu Glu Ile Pro Glu Glu Tyr Leu Glu Ala Ala Ala Lys Cys Har Gly Asp Trp Pro Cys Example 4

Figure 4:
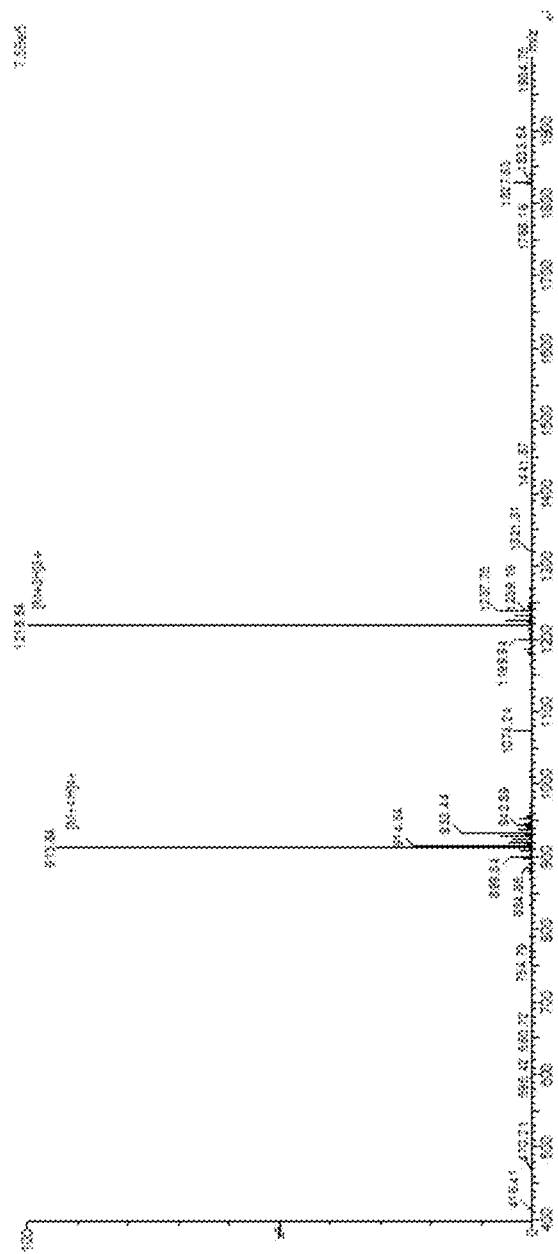
FIG. 4 shows detection results of mass spectrometry of polypeptide 4.

Polypeptide 4 was prepared in the same manner as Example 1, except that the L' fragment was Arg Val Leu Ala Glu Ala to obtain polypeptide 4 in a product weight of 0.86 g. Detection results of mass spectrometry of polypeptide 4 are shown in FIG. 4.

Polypeptide 4 has a structural formula as shown below (a polypeptide sequence shown in SEQ ID No. 7): D-Phe Pro Arg Pro Gly Gly Gly Gly Asn Gly Asp Phe Glu Glu Ile Pro Glu Glu Tyr Leu Glu Ala Ala Ala Lys Cys Har Gly Asp Trp Pro Cys Test Examples 1-4

Test examples 1 to 4 are used to demonstrate the anticoagulant and antiplatelet aggregation effect of polypeptides 1 to 4 prepared in Examples 1 to 4 on human blood. 30 ml of venous blood was drawn from a healthy volunteer, quickly injected into a plastic tube containing 3 ml of 3.8% sodium citrate solution, and then gently mixed by inversion up and down. The drawn blood was centrifuged at 810 rpm for 8 minutes to obtain platelet rich plasma (PRP), which was taken out, then the blood sample was further centrifuged at 3510 rpm for 8 minutes to obtain platelet poor plasma (PPP).

1. Determination of prothrombin time (PT), thrombin time (TT), activated partial thromboplastin time (APTT): Reagent reconstruction and preservation were performed according to the operation requirements of the kit. For each of the PPP, 10 samples to be detected were placed into test cups respectively, and individually added with physiological saline, polypeptide 1, polypeptide 2, polypeptide 3 or polypeptide 4, 10 μL per sample, and further added with PT, TT, APTT reagents, immediately before the test started. The effect of polypeptides 1-4 on human blood coagulation in vitro is shown in Table 3 (n represents the number of cases).

TABLE 3

Effect of polypeptides 1-4 on human blood coagulation in vitro

| Test samples | Concentration (mol/L) | PT(S) | Fold of Prolongation in PT | APTT(S) | Fold of Prolongation in APTT | TT(S) |
|---|---|---|---|---|---|---|
| Physiological saline | 0 | 11.22 | — | 33.10 | — | 14.07 |
| Polypeptide 1 (n = 16) | $1 \times 10^{-6}$ | 25.86 | 2.30 | 87.51 | 2.87 | >180 |
| Polypeptide 2 (n = 7) | $1 \times 10^{-6}$ | 34.78 | 3.04 | 104.14 | 3.35 | >180 |
| Polypeptide 3 (n = 3) | $1 \times 10^{-6}$ | 25.67 | 2.14 | 101.97 | 2.94 | >180 |
| Polypeptide 4 (n = 3) | $1 \times 10^{-6}$ | 58.93 | 4.92 | 98.85 | 2.57 | >180 |

The results in Table 3 show that, all of the four polypeptides 1 to 4 can affect human blood coagulation in vitro, and prolong the PT. APTT and TT to different extents. Among these compounds at a final concentration of $1 \times 10^{-6}$ mol/L, polypeptide 2 prolonged the PT and APTT in the largest fold.

2. Determination of platelet aggregation: A platelet aggregation instrument was started up and preheated for 30 minutes, and then calibrated with PPP. Into the test cups 270 μl of PRP was added, and then 10 μl of polypeptide 1, polypeptide 2, polypeptide 3 or polypeptide 4 ($1.0 \times 10^{-7}$ mol/L) and/or 20 μl of physiological saline were added respectively, till a total volume of 300 μl. After incubation for 5 min, 5 μl of inducer ADP and 5 μl of epinephrine were added to start the test. After 5 minutes, the test was completed, and the maximum aggregation rate within the 5 minutes was recorded, and the data and maps were printed. Based on the test results, the inhibitory rates of polypeptides 1-4 at different concentrations on platelet aggregation in human were calculated according to calculation equation 1, and the effect of polypeptides 1-4 on the ADP-induced human platelet aggregation in vitro is listed in Table 4. The calculation equation 1 is as follows:

Inhibitory rate of platelet aggregation =

$$\left(\frac{\text{Platelet aggregation rate before administration} - \text{Platelet aggregation rate after administration}}{\text{Platelet aggregation rate before administration}}\right) \times 100\%$$

TABLE 4

Effect of polypeptides 1-4 on ADP-induced human platelet aggregation in vitro

| Test samples | Concentration (mol/L) | Platelet aggregation rate (%) | Inhibitory rate of platelet aggregation (%) |
|---|---|---|---|
| Physiological saline | — | 73.39 | — |
| Polypeptide 1 (n = 8) | $3 \times 10^{-6}$ | 39.10 | 47.07 |
| Polypeptide 2 (n = 7) | $3 \times 10^{-6}$ | 26.12 | 66.70 |
| Polypeptide 3 (n = 3) | $3 \times 10^{-6}$ | 57.85 | 26.35 |
| Polypeptide 4 (n = 3) | $3 \times 10^{-6}$ | 61.28 | 18.88 |
| Polypeptide 1 (n = 8) | $1 \times 10^{-5}$ | 4.90 | 92.04 |
| Polypeptide 2 (n = 7) | $1 \times 10^{-5}$ | 0 | 100 |
| Polypeptide 3 (n = 3) | $1 \times 10^{-5}$ | 35.40 | 47.07 |
| Polypeptide 4 (n = 3) | $1 \times 10^{-5}$ | 54.80 | 27.97 |

The results in Table 4 show that, all of the four compounds, polypeptide 1, polypeptide 2, polypeptide 3 and polypeptide 4, can affect ADP-induced human platelet aggregation in vitro. Integrilin at a final concentration of $3 \times 10^{-6}$ mol/L can completely inhibit ADP-induced human platelet aggregation in vitro, with an inhibitory rate of 100%, and among the four compounds, polypeptide 1, polypeptide 2, polypeptide 3, polypeptide 4, at final concentrations of $3 \times 10^{-6}$ mol/L and $1 \times 10^{-5}$ mol/L, polypeptide 2 showed a strongest inhibition on ADP-induced human platelet aggregation in vitro.

Test Example 5

This test example is used to demonstrate the antithrombotic effect of polypeptide 2 prepared in EXAMPLE 2 in rats.

1. Experimental animals: 160 healthy, adult male SD rats, with body weight of 250 g ~300 g, purchased from Beijing Vital River Co., Ltd. Animal production license number: SCXK (Beijing) 2012-0001.

2. Samples to be tested: polypeptide 2 with a peptide content of 97.21%. Enoxaparin Sodium Injection, Aventis Intercontinental, Sanofi (Beijing) Pharmaceutical Co., Ltd., Subpackaging Approval Number: State medicine approval number: J20090094. Lot number: 2SN76, 0.4 ml: 4000 AxaIU×2 vials. Bivalirudin for Injection, Xi'an Xintong Pharmaceutical Research Co., Ltd., with a molecular weight of 2180.2, a purity of 96.55%, and a content of 69.44%.

3. Experimental Method
3.1 Formulation of Reagents and Preparation of Materials
3.1.1 Formulation of Reagents
3.1.1.1 Formulation of polypeptide 2 test solution: 200 mg of polypeptide 2 was accurately weighed and 10 mg/mL stock solution was prepared with physiological saline. An appropriate amount of the stock solution was taken to formulate the required dose according to the body weight of the animals, before the experiment every day.

3.1.1.2 Formulation of 20% urethane solution: 20 g of urethane was accurately weighed and metered with distilled water to a volume of 100 ml.

3.1.1.3 Formulation of 3.8% sodium citrate solution: 4.33 g of sodium citrate dihydrate was accurately weighed and metered with physiological saline to a volume of 100 ml, to obtain a 3.8% solution for use.

3.1.2 Preparation of Materials
3.1.2.1 Aluminum foil: The foil was measured with a ruler and cut to 2.5 cm×2.5 cm, numbered and weighed.
3.1.2.2 Preparation of 35% ferric chloride solution: 35 g of ferric chloride was taken and dissolved in 100 mL distilled water.

3.2 Grouping and Administration

160 Rats were randomly divided into groups, 5 to 10 rats per group. 1) Model control group: intravenous injection of the same volume of physiological saline; 2) 6 dose groups of polypeptide 2: starting from 1.5 mg/kg+3.75 mg/kg/h, which was decreased to 1 mg kg+2.5 mg/kg/h, 0.5 mg/kg+1.25 mg/kg/h, 0.25 mg/kg+0.75 mg/kg/h, 0.125 mg/kg+0.375 mg/kg/h, and 0.041 mg/kg+0.125 mg/kg/h; 3) 5 dose groups of positive control enoxaparin: starting from 30 U/kg+45 U/kg/h, which was increased to 60 U/kg+60 U/kg/h, 30 U/kg+120 U/kg/h, 90 U/kg+120 U/kg/h, 60 U/kg+240 U/kg/h, 4) 5 dose groups of positive control bivalirudin: starting from 0.5 mg/kg+2 mg/kg/h, which was decreased to 0.35 mg/kg+1.3 mg/kg/h, 0.17 mg/kg+0.65 mg/kg/h, 0.08 mg/kg+0.325 mg/kg/h. The animals were fasted with access to water 12 hours before the experiment (as shown in Table 5).

According to the body weight in kilograms of the rats, the first dose of a drug was dissolved in 2 mL of physiological saline for single bolus injection. The maintaining dose of drug was dissolved in 9 ml of physiological saline, and placed in a double-channel micro-injection pump, which was dripped off within 90 minutes at a dripping speed of 0.1 ml/min. The sham operation group was administered with the same volume of physiological saline.

4. Experimental Operation
4.1 Surgery Preparation of Rats

The rats were fasted with free access to water overnight before the experiment. The rats were anesthetized with intravenous injection of a 20% urethane solution at 5 ml/kg, fixed in the supine position, and then, the bilateral common carotid arteries, external jugular veins and inferior vena cava were isolated. The external jugular vein was subjected to intubation for administration; the common carotid artery on one side was subjected to intubation for blood collection to determine the blood coagulation functions PT and APTT, and the common carotid artery on the other side was used for the establishment of an arterial thrombosis model; and the inferior vena cava was used for the establishment of a venous thrombosis model.

4.2 Determination of Blood Coagulation Function

The blood samples were taken before administration, administration for 60 minutes, and before termination of administration, respectively, to determine their activated partial thromboplastin time (APTT) and prothrombin time (PT). The blood samples were centrifuged at 3510 rpm for 8 minutes to obtain platelet poor plasma (PPP). Reagent reconstruction and preservation were performed according to the operation requirements of the kit. Immediately after each blood sample was placed into a test cup and then PT and APTT reagents were added, the test was started. After the test was completed, results were recorded.

4.3 Arterial Thrombosis Model

After administration at a load dosage maintenance for 30 minutes, a filter paper with a 3 mm diameter and immersed with 35% FeCl$_3$ solution was applied below the common carotid artery, below which a small piece of a plastic film (2.5 cm×2.0 cm) was placed to protect surrounding tissues. The body temperature was detected with a temperature probe in the distal end of the artery, and the time required from the beginning of stimulation to the point when the temperature decreased by 2.5 degrees was examined as the vascular occlusion time.

4.4 Venous Thrombosis Model

After administration at a load dosage maintenance for 30 minutes, a filter paper with a 3 mm diameter and immersed with 35% FeCl$_3$ solution was applied below the inferior vena cava, below which a small piece of a plastic film (2.5 cm×2.0 cm) was placed to protect surrounding tissues. 15 minutes later, the filter paper was removed. And then, after observation for 45 minutes, the blood vessels and local tissues were rinsed with warm physiological saline, and the covered blood vessels were cut off. The thrombus which attached to the blood vessel walls was peeled off to be weighed on a tin foil for its wet weight, and then weighed overnight at room temperature for its dry weight. The administration was continued until the completion of the experiment.

5. Test Indicators 5.1 Determination of blood coagulation function: The blood samples were taken 0 min before administration, administration for 60 minutes, and termination of administration, respectively, and then determined using a platelet-aggregation coagulation factor analyzer for the blood coagulation functions (PT. APTT) and ACT.

5.2 Occlusion Time

The time from the point when FeCl$_3$ was placed to the point when the temperature of the artery indicated a decrease of 2.5° C. was the vascular occlusion time, which reflected the state of thrombus formation.

5.3 Thrombus Weight

After the experiment was completed, the segment of the blood vessels in which there had been thrombus formation was cut off, weighed for the wet weight, and then weighed overnight at room temperature for the dry weight of the thrombus. Thrombosis inhibitory rate was calculated.

TABLE 5

Dose grouping of polypeptide 2 and control drugs

| No. | Group | Dose (mg/kg + mg/kg/h) | n |
|---|---|---|---|
| 1 | Model | — | 10 |
| 2 | Enoxaparin group 1 | 30 + 45 u | 6 |
| 3 | Enoxaparin group 2 | 60 + 60 u | 5 |
| 4 | Enoxaparin group 3 | 30 + 120 u | 5 |
| 5 | Enoxaparin group 4 | 90 + 120 u | 6 |
| 6 | Enoxaparin group 5 | 60 + 240 u | 10 |
| 7 | Bivalirudin group 1 | 0.08 + 0.325 | 6 |
| 8 | Bivalirudin group 2 | 0.17 + 0.65 | 6 |
| 9 | Bivalirudin group 3 | 0.35 + 1.3 | 8 |
| 10 | Bivalirudin group 4 | 0.5 + 2 | 5 |
| 11 | Polypeptide 2 group 1 | 0.041 + 0.125 | 10 |
| 12 | Polypeptide 2 group 2 | 0.125 + 0.375 | 10 |
| 13 | Polypeptide 2 group 3 | 0.25 + 0.75 | 9 |
| 14 | Polypeptide 2 group 4 | 0.5 + 1.25 | 10 |
| 15 | Polypeptide 2 group 5 | 1 + 2.5 | 9 |
| 16 | Polypeptide 2 group 6 | 1.5 + 3.75 | 10 |

TABLE 6

Effect of intravenous maintenance administration of polypeptide 2 and control drugs at different dosages on FeCl$_3$-induced thrombosis in rats ($\bar{x} \pm s$)

| | Inferior vena cava thrombosis | | Common carotid arterial thrombosis | |
|---|---|---|---|---|
| | Thrombus | Inhibition | | |
| No. | weight (mg) | percentage (%) | OT (min) | Fold of prolongation |
| 1 | 22.54 ± 2.60 | — | 22.54 ± 2.60 | — |
| 2 | 14.67 ± 8.44* | 34.93 | 48.17 ± 13.12** | 1.93 ± 0.52 |
| 3 | 11.18 ± 4.47** | 50.42 | 55.75 ± 7.23** | 2.23 ± 0.29 |
| 4 | 11.48 ± 2.81** | 49.07 | 41.4 ± 6.68** | 1.66 ± 0.27 |
| 5 | 8.10 ± 3.67** | 64.06 | 48.83 ± 11.58** | 1.95 ± 0.46 |
| 6 | 6.59 ± 2.54** | 86.25 | 49.75 ± 5.04** | 1.99 ± 0.20 |
| 7 | 18.03 ± 1.39* | 20.03 | 44.75 ± 1.53** | 1.79 ± 0.06 |
| 8 | 14.43 ± 3.84** | 35.97 | 56.00 ± 6.03** | 2.24 ± 0.24 |
| 9 | 7.06 ± 4.07** | 68.67 | 55.63 ± 8.21** | 2.23 ± 0.33 |
| 10 | 7.26 ± 3.15** | 67.79 | 58.00 ± 5.77** | 2.32 ± 0.23 |
| 11 | 20.20 ± 10.00 | 10.38 | 20.20 ± 10.00 | 10.38 |
| 12 | 16.23 ± 6.76* | 27.99 | 16.23 ± 6.76* | 27.99 |
| 13 | 14.23 ± 4.82** | 36.85 | 14.23 ± 4.82** | 36.85 |
| 14 | 9.25 ± 4.86** | 58.96 | 9.25 ± 4.86** | 58.96 |
| 15 | 9.91 ± 6.20** | 56.03 | 9.91 ± 6.20** | 56.03 |
| 16 | 7.13 ± 3.46** | 68.37 | 7.13 ± 3.46** | 68.37 |

TABLE 7

Effect of intravenous maintenance administration of polypeptide 2 and control drugs at different dosages on blood coagulation function in rats ($\bar{x} \pm s$)

| Group | Dose | n | Before administration | APTT administration for 60 minutes | Fold of change |
|---|---|---|---|---|---|
| Model | — | 10 | 28 ± 6.18 | 29.54 ± 6.58 | 1.18 ± 0.51 |
| Enoxaparin group 1 | 30 + 45 u | 6 | 28.99 ± 7.00 | 52.28 ± 22.51 | 1.78 ± 0.61 |
| Enoxaparin group 2 | 60 + 60 u | 5 | 23.45 ± 4.70 | 61.81 ± 13.19 | 2.66 ± 0.36 |
| Enoxaparin group 3 | 30 + 120 u | 5 | 23.66 ± 5.88 | 117.55 ± 78.85 | 4.65 ± 1.72 |
| Enoxaparin group 4 | 90 + 120 u | 6 | 19.04 ± 5.26 | 270.85 ± 148.90 | 16.34 ± 12.97 |
| Enoxaparin group 5 | 60 + 240 u | 10 | 26.79 ± 4.74 | 270.43 ± 166.43 | 10.69 ± 7.14 |
| Bivalirudin group 1 | 0.08 + 0.325 | 6 | 25.05 ± 1.78 | 34.18 ± 12.92 | 1.36 ± 0.50 |
| Bivalirudin group 2 | 0.17 + 0.65 | 6 | 25.55 ± 5.02 | 41.46 ± 14.96 | 1.66 ± 0.60 |
| Bivalirudin group 3 | 0.35 + 3.3 | 8 | 23.16 ± 2.37 | 95.86 ± 45.71 | 4.10 ± 1.86 |

TABLE 7-continued

Effect of intravenous maintenance administration of polypeptide 2 and control drugs at different dosages on blood coagulation function in rats ($\bar{x} \pm s$)

| Bivalirudin group 4 | 0.5 + 2 | 5 | 24.77 ± 7.84 | 90.23 ± 21.92 | 3.89 ± 1.37 |
| --- | --- | --- | --- | --- | --- |
| Polypeptide 2 group 1 | 0.041 + 0.125 | 10 | 24.54 ± 5.09 | 37.29 ± 10.59 | 1.65 ± 0.84 |
| Polypeptide 2 group 2 | 0.125 + 0.375 | 10 | 24.05 ± 5.44 | 44.55 ± 12.74 | 1.94 ± 0.68 |
| Polypeptide 2 group 3 | 0.25 + 0.75 | 9 | 24.98 ± 5.11 | 53.13 ± 22.57 | 2.22 ± 1.12 |
| Polypeptide 2 group 4 | 0.5 + 1.25 | 10 | 22.03 ± 4.70 | 52.29 ± 25.87 | 2.49 ± 1.38 |
| Polypeptide 2 group 5 | 1 + 2.5 | 9 | 23.98 ± 6.83 | 108.52 ± 56.27 | 5.01 ± 3.00 |
| Polypeptide 2 group 6 | 1.5 + 3.75 | 10 | 23.94 ± 4.49 | 74.62 ± 49.41 | 3.19 ± 2.02 |

| | | | PT | | |
| --- | --- | --- | --- | --- | --- |
| Group | Dose | n | Before administration | administration for 60 minutes | Fold of change |
| Model | — | 10 | 31.38 ± 3.00 | 12.32 ± 1.59 | 1.08 ± 0.40 |
| Enoxaparin group 1 | 30 + 45 u | 6 | 10.23 ± 1.19 | 12.70 ± 2.49 | 1.24 ± 0.14 |
| Enoxaparin group 2 | 60 + 60 u | 5 | 9.53 ± 1.96 | 31.39 ± 35.50 | 4.10 ± 5.56 |
| Enoxaparin group 3 | 30 + 120 u | 5 | 9.93 ± 1.77 | 16.17 ± 1.86 | 1.67 ± 0.42 |
| Enoxaparin group 4 | 90 + 120 u | 6 | 9.63 ± 1.58 | 14.88 ± 1.67 | 1.57 ± 0.21 |
| Enoxaparin group 5 | 60 + 240 u | 10 | 10.28 ± 0.98 | 18.21 ± 2.70 | 1.78 ± 0.30 |
| Bivalirudin group 1 | 0.08 + 0.325 | 6 | 10.42 ± 1.16 | 18.95 ± 3.36 | 1.82 ± 0.24 |
| Bivalirudin group 2 | 0.17 + 0.65 | 6 | 11.16 ± 1.28 | 21.85 ± 7.38 | 1.99 ± 0.78 |
| Bivalirudin group 3 | 0.35 + 1.3 | 8 | 11.73 ± 1.48 | 42.58 ± 21.94 | 3.54 ± 1.45 |
| Bivalirudin group 4 | 0.5 + 2 | 5 | 7.87 ± 1.93 | 39.13 ± 7.30 | 4.46 ± 1.47 |
| Polypeptide 2 group 1 | 0.041 + 0.125 | 10 | 10.74 ± 3.97 | 18.95 ± 8.65 | 1.95 ± 1.27 |
| Polypeptide 2 group 2 | 0.125 + 0.375 | 10 | 11.21 ± 1.62 | 19.00 ± 4.39 | 1.70 ± 0.34 |
| Polypeptide 2 group 3 | 0.25 + 0.75 | 9 | 11.19 ± 1.06 | 20.82 ± 5.66 | 1.87 ± 0.50 |
| Polypeptide 2 group 4 | 0.5 + 1.25 | 10 | 10.58 ± 1.48 | 26.07 ± 3.91 | 2.53 ± 0.73 |
| Polypeptide 2 group 5 | 1 + 2.5 | 9 | 10.53 ± 1.29 | 56.65 ± 23.16 | 5.57 ± 2.74 |
| Polypeptide 2 group 6 | 1.5 + 3.75 | 10 | 11.98 ± 1.02 | 46.64 ± 23.46 | 3.91 ± 1.89 |

As can be seen from the results of Tables 6 and 7, polypeptide 2 can dose-dependently inhibit $FeCl_3$-induced inferior vena cava thrombosis in rats, inhibit $FeCl_3$-induced common carotid arterial thrombosis in rats, and prolong APTT and PT in rats.

Figure 5:
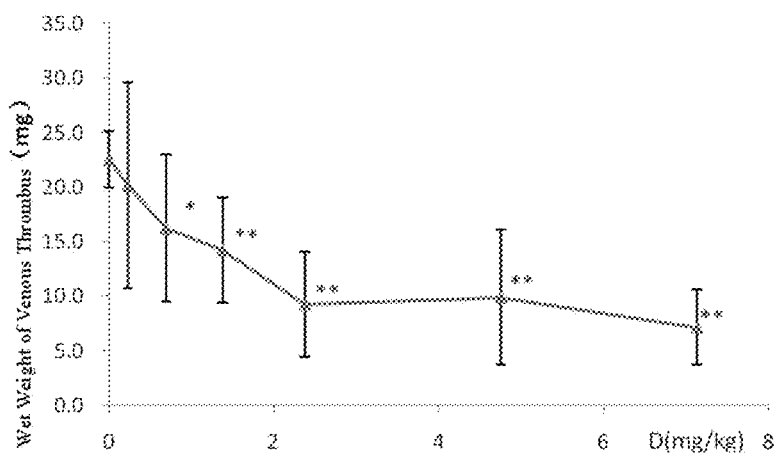
FIG. 5 shows effect of polypeptide 2 on $FeCl_3$-induced inferior vena cava thrombosis in rats.
Figure 6:
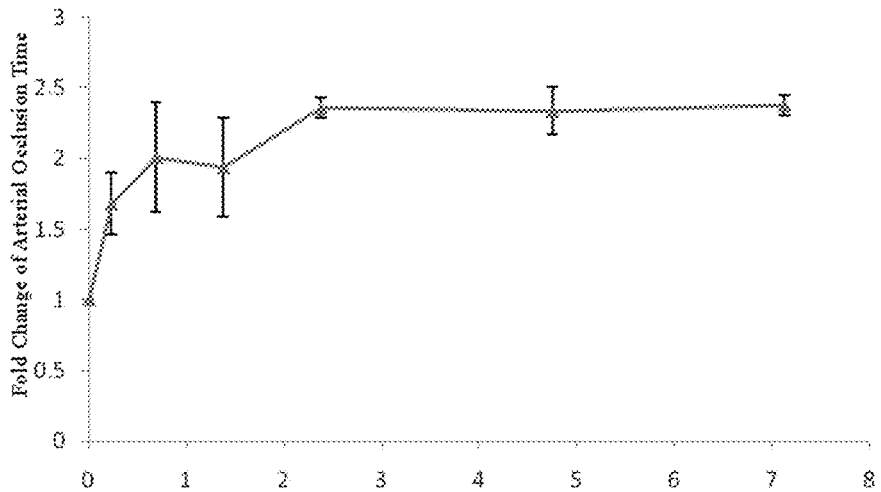
FIG. 6 shows effect of polypeptide 2 on $FeCl_3$-induced common carotid arterial thrombosis in rats.
Figure 7:
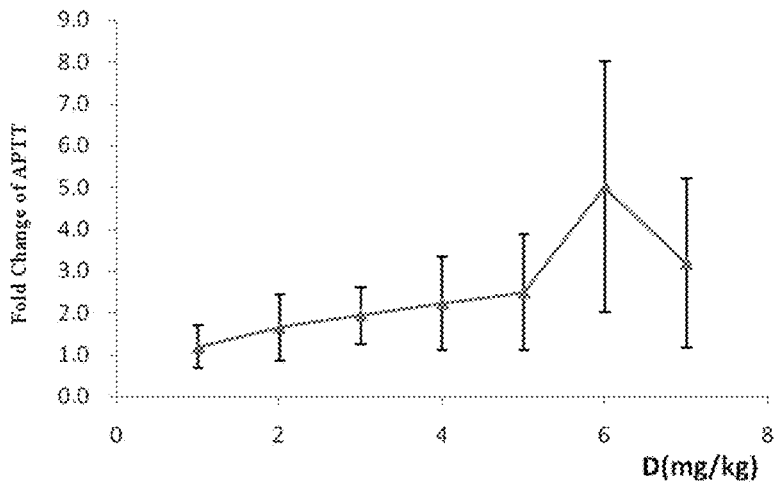
FIG. 7 shows effect of polypeptide 2 on APTT in rats.
Figure 8:
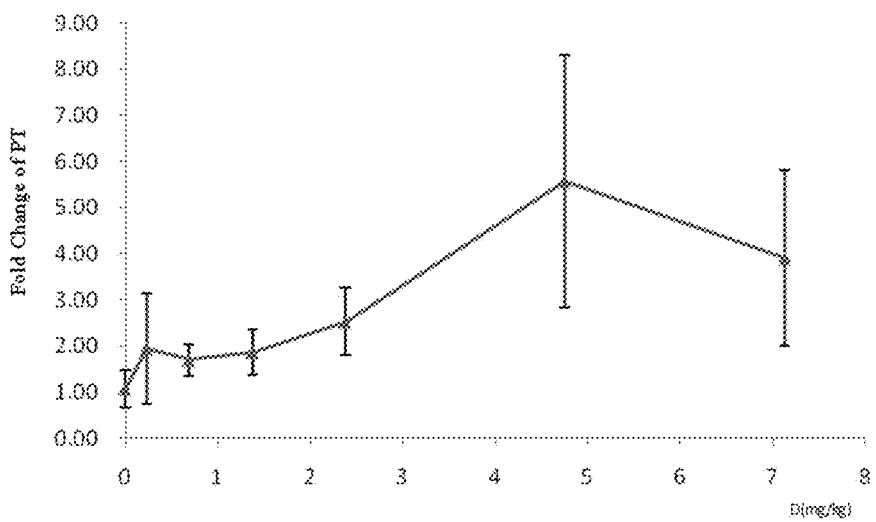
FIG. 8 shows effect of polypeptide 2 on PT in rats.

FIG. 5 shows effect of polypeptide 2 on $FeCl_3$-induced inferior vena cava thrombosis in rats, with *$P<0.05$, $P<0.01$ compared with the model group. FIG. 6** shows effect of polypeptide 2 on $FeCl_3$-induced common carotid arterial thrombosis in rats, which shows the fold of change in the arterial occlusion time, with *$P<0.05$, $P<0.01$ compared with the model group. FIG. 7 shows effect of polypeptide 2 on APTT in rats. FIG. 8** shows effect of polypeptide 2 on PT in rats.

Test Example 6

This test example is used to illustrate a pharmacodynamic test of thrombus inhibition in rabbits by intravenous maintenance administration of polypeptide 2 prepared in EXAMPLE 2.

1. Experimental Animals and Materials 1.1 Experimental animals: 10 healthy adult male rabbits, weighed to be 2 to 2.5 kg, provided by Xi'an Dilepu Biological Resources Development Co., Ltd., Animal production license number: SCXK (Shaanxi) 2006-001. Samples to be tested: polypeptide 2 having a peptide content of 97.21%. Positive control: Enoxaparin Sodium Injection, Aventis Intercontinental, Sanofi (Beijing) Pharmaceutical Co., Ltd., Subpackaging Approval Number: state medicine approval number: J20090094. Lot number: 2SN76, 0.4 ml: 4000 AxaIU×2 vials.

1.2 Experimental Materials are Shown in Table 8.

TABLE 8

| Name | Manufacturer | Specification | Lot No. |
| --- | --- | --- | --- |
| Sodium pentobarbital | US sigma Company | 25 g/bottle | 090205 |
| Sodium citrate | Tianjin Baishi Chemical Co., Ltd. | — | 20080418 |
| 0.9% NaCl injection | Xi'an Jingxi Shuanghe Pharmaceutical Co., Ltd. | 250 mL/bottle | 11806471 |
| Heparin sodium injection | Tianjin Biochemical Pharmaceutical Co., Ltd. | 2 mL 12500 IM | 20120202 |
| Diadenosine phosphate | SIGMA | 1 g/bottle | purchased on Dec. 10, 2009 |
| Adrenal hydrochloride injection | Shanghai Hefeng Pharmaceutical Co. Ltd | 1 mg/mL | 20090701 |
| PT Assay Kit | Shaanxi Ark Biotechnology Co., Ltd. | 10 × 2 ml | 20140703 |
| TT Assay Kit | Shaanxi Ark Biotechnology Co., Ltd. | 10 × 2 ml | 20140702 |
| APPT Assay Kit | Shaanxi Ark Biotechnology Co., Ltd. | 10 × 2 ml | 20140702 |

1.3 Formulation of polypeptide 2 test solution: 200 mg of polypeptide 2 was accurately weighed with an electronic balance and was prepared into 10 mg/mL stock solution with physiological saline, which was sufficiently mixed well, sub-packaged in 5 mL for each, and stored at −20° C. During the test, an appropriate amount of the stock solution was diluted and used by calculation based on the body weight of the rabbits.

3% Sodium pentobarbital solution: 3 g of sodium pentobarbital was accurately weighed and metered with distilled water to a volume of 100 ml.

3.8% Sodium citrate solution: 4.33 g of sodium citrate dihydrate was accurately weighed and metered with physiological saline to a volume of 100 ml, to obtain a 3.8% solution for use.

Epinephrine solution: 1.319 ml of stock solution was taken and metered to 100 ml with physiological saline to prepare a 60 μM solution, which was stored at 4° C. in a refrigerator and sub-packaged before use.

ADP solution: 14.3 mg of ADP was accurately weighed and dissolved in 5 ml of physiological saline to obtain a 6000 μmol/L ADP solution which was stored at 4° C., and was diluted with physiological saline to 600 μmol/L before the experiment.

1.4 Preparation of Materials

Aluminum foil: The foil was measured with a ruler and cut to 2.5 cm×2.5 cm, numbered and weighed; nonabsorbable surgical suture: 8 cm long of the suture was taken with a ruler and weighed.

50% ferric chloride solution: 50 g of ferric chloride was taken and dissolved in 100 mL of distilled water.

2. Grouping and administration: 10 rabbits were randomly divided into 3 groups, 2 to 3 rabbits per group. 1) Sham operation group (NS): Intravenous injection of the same volume of physiological saline, with the same operation method as above; 2) polypeptide 2 administration group: 8.0 mg/kg+20.0 mg/kg/h; 3) positive control enoxaparin group: 50 U/kg+150 U/kg/h. According to the body weight in kilograms of the rabbits, the first dose of the drug to be tested was dissolved in 2 mL of physiological saline for single bolus injection. The maintaining dose was dissolved in 9 ml of physiological saline, and placed in a double-channel micro-injection pump, which was dripped off within 90 minutes at a dripping speed of 1 ml/min. The sham operation group was administered with the same volume of physiological saline.

3. Experimental Operation 3.1 Surgery preparation of rabbits: Rabbits were sent to the laboratory for accommodation for one day, and then screened at first. Blood samples were taken from arteries within ears, which were subjected to blood routine analysis and APTT assay, and the rabbits with normal blood hemateikon and APTT between 16s to 28s were selected for experiments. The rabbits to be tested were fasted with free access to water for the night before the experiment. The rabbits were anesthetized with intravenous injection of 3% sodium pentobarbital solution at 1 ml/kg, fixed in the supine position, and then, the common carotid artery at one side, external jugular vein, femoral artery at one side, femoral vein, and forelimb vein at one side were isolated. The forelimb vein was subjected to intubation for administration; the left femoral vein was subjected to intubation for blood collection to determine the platelet aggregation rate; the femoral artery was used for the establishment of an arterial thrombosis model; the common carotid artery and external jugular vein were used for the establishment of an arterial and venous bypass thrombosis model.

3.2 Arterial thrombosis (AT) model: A small piece of a filter paper (1 cm×1.5 cm) absorbed with 50% FeCl$_3$ solution was applied onto the right femoral artery while administration, below which a small piece of a plastic film (2.5 cm×2.0 cm) was placed to protect surrounding tissues. After 10 minutes, the filter paper was removed, and then, the blood vessels and local tissues were rinsed with warm physiological saline, and the covered blood vessels were cut off. The thrombus which attached to the blood vessel walls was peeled off to be weighed on a tin foil for its wet weight, and then kept overnight at room temperature and weighed for its dry weight.

3.3 Experimental Procedures: The femoral arteries in the forelimb and both sides in the rabbits were isolated and stabilized for 10 minutes before the administration was started. An AT model was established by covering the femoral artery with a 50% FeCl$_3$ filter paper while administration, and the filter paper was removed after 15 minutes. Observation was continued for 120 min after administration until the experiment was completed.

4. Test Indicators 4.1 Platelet aggregation rate: At points of 0 min before administration; 30 min. 60 min, 90 min for administration; 60 min, 120 min, 180 min after administration was terminated, 2.7 ml blood samples were taken from the femoral vein, rapidly injected into a centrifuge tube containing 0.3 ml of 3.8% sodium citrate solution, and fully mixed well. The resulted blood samples were centrifuged at 810 rpm (100 g) for 8 min to obtain PRP, and was centrifuged at 3500 rpm (1863 g) for 8 min to obtain PPP which was used to determine platelet aggregation.

Blood samples were taken before administration (0 min), 5 min and 15 min after administration, respectively, to determine the platelet aggregation rate which was used to calculate the inhibitory rate of platelet aggregation with a calculation equation as follows:

$$\text{Inhibitory rate of platelet aggregation} = \frac{\left(\begin{array}{l}\text{Platelet aggregation rate before administration}- \\ \text{Platelet aggregation rate after administration}\end{array}\right)}{\text{Platelet aggregation rate before administration}} \times 100\%$$

4.2 Determination of blood coagulation function: Blood samples were taken and the blood function (PT, APTT) was determined at 0 min before administration, at points of 30 min, 60 min, 90 min after administration, and at points of 60 min, 120 min and 180 min after termination of administration, using a platelet-aggregation coagulation factor analyzer. Blood samples were centrifuged at 3510 rpm for 8 min to obtain platelet poor plasma (PPP). Reagent reconstruction and preservation were performed according to the operation requirements of the kit. Immediately after each blood sample was placed into a test cup and then added with PT, TT and APTT reagents, the test was started. After the test was completed, results were recorded.

4.3 Determination of ACT: At 0 min before administration and at points of administration for 5 min and 15 min, the whole blood was taken, to which kaolin was added, and placed in a water bath at 37° C. to record the whole blood coagulation time.

4.4 Thrombus weight: After the experiment was completed, the segment of the blood vessels in which there had been thrombus formation was cut off, weighed for the wet weight, and then kept overnight at room temperature and weighed for the dry weight. The thrombosis inhibitory rate was calculated with a calculation equation as follows:

$$\text{Thrombosis inhibitory rate} = \left(\frac{\text{Thrombus weight before administration} - \text{Thrombus weight after administration}}{\text{Thrombus weight before administration}}\right) \times 100\%$$

5. Test Results:

5.1 Effect of Intravenous Maintenance Administration of Polypeptide 2 on FeCl$_3$-Induced Femoral Artery Thrombosis in Rabbits The results show the effect of polypeptide 2 at 8.0 mg/kg+20.0 mg/kg/h on FeCl$_3$-induced femoral artery thrombosis in rabbits, in which the thrombosis inhibitory rate of enoxaparin at 50 U/kg+150 U/kg/h is lower than that of polypeptide 2, which has no statistic difference (P>0.05) compared with the physiological saline group. The results are shown in Table 9.

TABLE 9

Effect of intravenous maintenance administration of polypeptide 2 on femoral artery thrombosis in rabbits ($\bar{x} \pm s$)

| Group | Dose (mg/kg + mg/kg/h) | n | Thrombus weight (mg) Wet weight | Dry weight | Thrombus inhibitory rate (%) Wet weight | Dry weight |
|---|---|---|---|---|---|---|
| Blank group | — | 3 | 58.2 ± 11.2 | 20.9 ± 5.9 | — | — |
| Enoxaparin | 50 U + 150 U | 2 | 3.9 ± 4.0 | 2.3 ± 2.1 | 40 ± 5.7 | 10 ± 4.2 |
| Polypeptide 2 | 8.0 + 20.0 | 4 | 14.2 ± 10.2 | 3.2 ± 2.0 * | 75.6 ± 3.8 | 84.9 ± 2.3 |

5.2 Effect of Intravenous Maintenance Administration of Polypeptide 2 on Platelet Aggregation Function in Rabbits The results show that, the intravenous maintenance administration of polypeptide 2 can inhibit platelet aggregation in rabbits. After the administration was terminated, the inhibition of platelet aggregation was gradually weakened over time. The inhibitory rate of platelet aggregation by enoxaparin at 50 U/kg+150 U/kg/h is lower than that of polypeptide 2. The results are shown in Table 10.

TABLE 10

Effect of single intravenous administration of polypeptide 2 on platelet aggregation function in rabbits (inhibitory rate of platelet aggregation, %, $\bar{x} \pm s$)

| Group | Dose (mg/kg + mg/kg/h) | n | Administration for 30 min | Administration for 60 min | Administration for 90 min |
|---|---|---|---|---|---|
| Blank group | — | 2 | 12.1 ± 17.1 | 12.1 ± 17.1 | 13.1 ± 18.6 |
| Enoxaparin | 50 U + 150 U | 1 | 26.7 | 0.00 | 35.27 |
| Polypeptide 2 | 8.0 + 20.0 | 2 | 61.0 ± 14.1 | 72.1 ± 9.6 | 55.8 ± 7.7 |

| Group | Dose (mg/kg + mg/kg/h) | n | 60 min after termination | 120 min after termination | 180 min after termination |
|---|---|---|---|---|---|
| Blank group | — | 2 | 22.1 ± 31.2 | 13.9 ± 19.7 | — |
| Enoxaparin | 50 U + 150 U | 1 | 0.00 | 41.9 | — |
| Polypeptide 2 | 8.0 + 20.0 | 2 | 14.1 ± 3.5 | 7.5 ± 1.8 | 47.5 ± 2.5 |

5.3 Effect of Intravenous Maintenance Administration of Polypeptide 2 on Blood Coagulation Function in Rabbits The results are shown in Tables 11-14. Table 11 shows the effect of intravenous maintenance administration of polypeptide 2 on the blood coagulation function APTT in rabbits (S, ($\bar{x}\pm s$)); Table 12 shows the effect of intravenous maintenance administration of polypeptide 2 on the blood coagulation function PT in rabbits (S, ($\bar{x}\pm s$)); Table 13 shows the effect of intravenous maintenance administration of polypeptide 2 on the blood coagulation function TT in rabbits (S, ($\bar{x}\pm s$)); and Table 14 shows the effect of intravenous maintenance administration of polypeptide 2 on ACT in rabbits (S, ($\bar{x}\pm s$)). In Tables 11-14, the dose unit is (mg/kg+mg/kg/h). The results show that the intravenous maintenance administration of polypeptide 2 can inhibit platelet aggregation in rabbits. After the administration was terminated, the inhibition of platelet aggregation was gradually weakened over time.

TABLE 11

| Group | Dose | n | Before administration | Administration (min) 30 | 60 | 90 | Termination (min) 60 | 120 | 180 |
|---|---|---|---|---|---|---|---|---|---|
| Blank | — | 2 | 24.3 ± 4.4 | 22.7 ± 1.6 | 20.4 ± 1.9 | 20.2 ± 0.4 | 19.9 ± 1.0 | 35.0 ± 8.3 | ± |
| Enoxaparin | 50 U + 150 U | 1 | 25.7 | 32.4 | 36.2 | 38.3 | 30.5 | 62.1 | 41.6 |
| Polypeptide 2 | 8.0 + 20.0 | 2 | 22.7 ± 1.7 | 38.0 ± 2.3 | 32.5 ± 1.0 | 34.1 ± 3.7 | 35.7 ± 14.0 | 33.2 ± 2.7 | 23.3 ± 1.6 |

TABLE 12

| Group | Dose | n | Before administration | Administration (min) 30 | 60 | 90 | Termination (min) 60 | 120 | 180 |
|---|---|---|---|---|---|---|---|---|---|
| Blank | — | 2 | 6.3 ± 0.8 | 7.0 ± 1.4 | 6.3 ± 2.5 | 6.1 ± 1.8 | 5.7 ± 0.6 | 5.9 ± 0.5 | ± |
| Enoxaparin | 50 U + 150 U | 1 | 9.4 | 10.4 | 10.4 | 11.3 | 8.2 | 8.1 | 7.6 |
| Polypeptide 2 | 8.0 + 20.0 | 2 | 7.7 ± 1.8 | 12.7 ± 0.5 | 9.4 ± 2.0 | 11.6 ± 1.3 | 7.7 ± 0.0 | 7.1 ± 1.8 | 7.4 ± 1.3 |

TABLE 13

| Group | Dose | n | Before administration | Administration (min) 30 | 60 | 90 | Termination (min) 60 | 120 | 180 |
|---|---|---|---|---|---|---|---|---|---|
| Blank | — | 2 | 21.1 ± 4.9 | 18.3 ± 2.4 | 17.3 ± 3.0 | 17.7 ± 2.7 | 15.6 ± 0.0 | 17.7 ± 2.1 | ± |
| Enoxaparin | 50 U + 150 U | 1 | 20.5 | >180 s | >180 s | 18.9 | 21.0 | 29.0 | 24.0 |
| Polypeptide 2 | 8.0 + 20.0 | 2 | 26.8 ± 15.5 | >180 s | >180 s | >180 s | >180 s | 150.6 ± 3.5 | 28.2 ± 1.9 |

TABLE 14

| Group | Dose | n | Before administration | Administration (min) 30 | 60 | 90 | Termination (min) 60 | 120 | 180 |
|---|---|---|---|---|---|---|---|---|---|
| Blank | — | 2 | 210.0 ± 21.2 | 180.0 ± 21.2 | 127.5 ± 31.8 | 127.5 ± 10.6 | 112.5 ± 74.2 | 165.0 ± 21.2 | ± |
| Enoxaparin | 50 U + 150 U | 1 | 180.0 | 225.0 | 375.0 | 270.0 | 210 | 195.0 | 225.0 |
| Polypeptide 2 | 8.0 + 20.0 | 2 | 217.5 ± 95.5 | 330.0 ± 63.6 | 277.5 ± 31.8 | 300.0 ± 63.6 | 180.0 ± 21.2 | 172.5 ± 31.8 | 112.5 ± 74.2 |

The above results show that, bolus injection (iv)+intravenous drip (vd) of polypeptide 2 for 90 minutes can inhibit platelet aggregation in rabbits, affect the blood coagulation function in rabbits, prolong APTT, PT, TT and ACT, and also inhibit femoral artery thrombosis. When polypeptide 2 and enoxaparin have the comparable effect to inhibit femoral artery thrombosis and to inhibit platelet aggregation, enoxaparin prolongs APTT more than polypeptide 2, indicating that the bleeding risk of enoxaparin is greater than that of polypeptide 2.

Test Example 7

This test example is used to illustrate antithrombotic as well as anticoagulant and antiplatelet aggregation experiments in vivo with single intravenous administration in rabbits. Experimental animals: 48 healthy adult male rabbits, weighed to be 2 to 2.5 kg, provided by Xi'an Dilepu Biological Resources Development Co., Ltd., Animal production license number: SCXK (Shaanxi) 2006-001. Samples to be tested: polypeptide 2 having a peptide content of 97.21%. Positive drugs: enoxaparin and bivalirudin.

[Experimental Method]

1. Grouping and administration: 48 Rabbits were randomly divided into 6 groups, 8 rabbits per group. 1) Sham operation group (NS): Intravenous injection of the same volume of physiological saline; 2) positive control bivalirudin group (6 mg/kg); 3) positive control enoxaparin group (200 U/kg); 4) Low dose group of polypeptide 2 (3.0 mg/kg); 5) Medium dose group of polypeptide 2 (6.0 mg/kg); 6) High dose group of polypeptide 2 (12.0 mg/kg). Polypeptide 2 was administered by single intravenous administration. According to the body weight in kilograms of the rabbits, the sample was dissolved in 2 mL of physiological saline for single bolus injection. The sham operation group was administered with the same volume of physiological saline.

2. Experimental Operation 2.1 Surgery preparation of rabbits: Rabbit were sent to the laboratory for accommodation for one day, and then screened at first. Blood samples were taken from arteries within ears, which were subjected to blood routine analysis and APTT examinations, and the rabbits with a normal blood hemogram and APTT between 16 and 28 seconds were selected for experiments. The rabbits to be tested were fasted with free access to water in the night before the experiment.

The rabbits were anesthetized with intravenous injection of 3% sodium pentobarbital solution at 1 ml/kg, fixed in the supine position, and then, the common carotid artery at one side, external jugular vein, femoral artery at one side, femoral vein, and forelimb vein at one side were isolated. The forelimb vein was subjected to intubation for administration; the left femoral vein was subjected to intubation for blood collection to determine the platelet aggregation rate; the femoral artery was used for the establishment of an arterial thrombosis model; the common carotid artery and external jugular vein were used for the establishment of an arterial and venous bypass thrombosis model.

2.2 Arterial and venous bypass thrombosis (AVST) model: An arterial and venous shunt consists of two casings, of which an outer casing has a length of about 8 cm and an inner diameter of 7.9 mm, the inner casing has a length of about 2.5 cm and an inner diameter of 4.8 mm. The polyethylene tube was charged with a silk thread about 8 cm long and filled with 50 M/ml heparin solution, of which one end was inserted into the left femoral artery and the other end was inserted into the right femoral vein. After administration for 30 seconds, the blood flow was released, which flowed from the left artery to the polyethylene tube and returned to the right vein. After 15 minutes, the blood flow was interrupted, the silk thread was quickly removed and placed on an aluminum foil (size: 2.5 cm×2.5 cm), measured for its wet weight, and kept overnight at room temperature and weighed for its dry weight.

2.3 Arterial thrombosis (AT) model: A small piece of filter paper (1 cm×1.5 cm) absorbed with 50% FeCl₃ solution was applied onto the right femoral artery while administration, below which a small piece of a plastic film (2.5 cm×2.0 cm) was placed to protect surrounding tissues. After 10 minutes, the filter paper was removed, and then, the blood vessels and local tissues were rinsed with warm physiological saline, and the covered blood vessels were cut off. The thrombus which attached to the blood vessel walls was peeled off to be weighed on a tin foil for its wet weight, and then kept overnight at room temperature and weighed for its dry weight.

Figure 9:
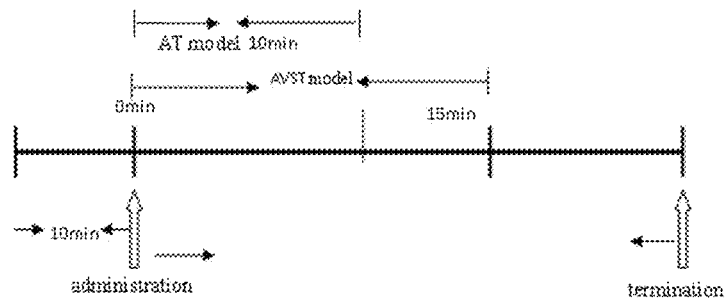
FIG. 9 is a flowchart of an arterial thrombosis model test.

2.4 Experimental Procedures: Experimental procedures are shown in FIG. 9. The femoral arteries in the forelimb and both sides in the rabbits were isolated and stabilized for 10 min before the administration was started. An AT model was established by covering the femoral artery with 50% FeCl₃ filter paper while administration, and the filter paper was removed after covering for 15 minutes. An AVST model was established and it was taken out after 40 minutes. Observation was continued for 120 min after administration until the experiment was completed.

3. Test Indicators 3.1 Platelet aggregation rate: 2.7 ml of blood was taken from the femoral vein, rapidly injected into a centrifuge tube containing 0.3 ml of 3.8% sodium citrate solution, and fully mixed well. The resulted blood samples were centrifuged at 810 rpm (100 g) for 8 min to obtain PRP, which was taken out and centrifuged at 3500 rpm (1863 g) for 8 min to obtain PPP, which was used to determine platelet aggregation.

Blood samples were taken at a point before administration (0 min), and at points of administration for 5 min and 15 min, respectively, to determine the platelet aggregation rate, which was used to calculate the inhibitory rate of platelet aggregation with a calculation equation as follows:

$$\text{Inhibitory rate of platelet aggregation} = \frac{\left(\begin{array}{c}\text{Platelet aggregation rate before administration} - \\ \text{Platelet aggregation rate after administration}\end{array}\right)}{\text{Platelet aggregation rate before administration}} \times 100\%$$

3.2 Determination of blood coagulation function: Blood samples were taken and the blood function (PT, TT, APTT) was determined at 0 min before administration, at points of 5 min and 15 min after administration, using a platelet-aggregation coagulation factor analyzer. Blood samples were centrifuged at 3510 rpm for 8 min to obtain platelet poor plasma (PPP). Reagent reconstruction and preservation were performed according to the operation requirements of the kit. Immediately after each blood sample was placed into a test cup and then added with PT. TT and APTT reagents, the test was started. After the test was completed, results were recorded.

3.3 Determination of ACT: At 0 min before administration and at points of administration for 5 min and 15 min, the whole blood was taken, to which kaolin was added, and placed in a water bath at 37° C. to record the whole blood coagulation time.

3.4 Thrombus weight: After the experiment was completed, the segment of the blood vessels in which there had been thrombus formation was cut off, weighed for the wet weight, and then kept overnight at room temperature and weighed for the dry weight. The thrombosis inhibitory rate was calculated with a calculation equation as follows:

$$\text{Thrombosis inhibitory rate} = \frac{\left(\begin{array}{c}\text{Thrombus weight before administration} - \\ \text{Thrombus weight after administration}\end{array}\right)}{\text{Thrombus weight before administration}} \times 100\%$$

4. Test Results:

4.1 Effect of Single Intravenous Administration of Polypeptide 2 on FeCl₃-Induced Femoral Artery Thrombosis in Rabbits.

Figure 10:
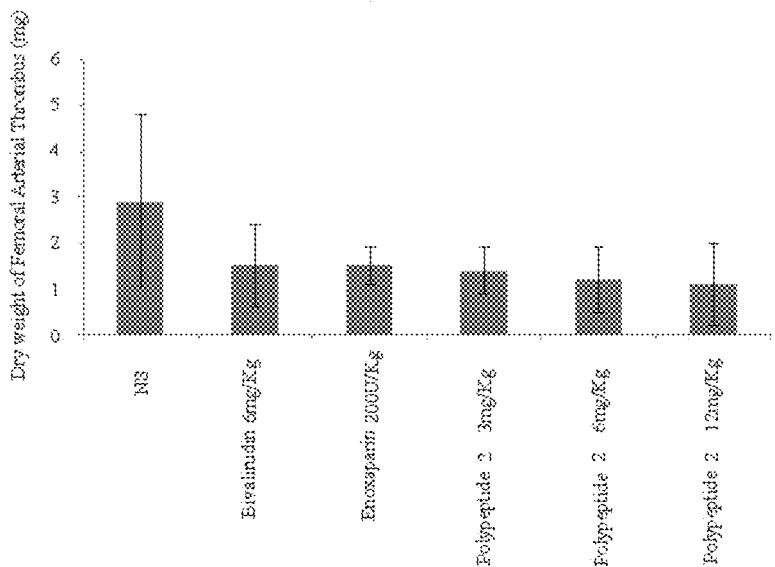
FIG. 10 shows effect of single intravenous administration of polypeptide 2 on the dry weight of thrombus of $FeCl_3$-induced femoral artery thrombosis in rabbits.

The results are shown in FIG. 10 and Table 15. Single intravenous administration of different concentrations of polypeptide 2 can reduce the dry weight of FeCl₃-induced femoral artery thrombus in rabbits and inhibit FeCl₃-induced femoral artery thrombosis in rabbits. Compared with the physiological saline group, there was a significant statistic difference (P<0.05) for the low dose group of polypeptide 2 in 3.0 mg/kg (P<0.05): there was a very significant statistic difference for the medium dose group of polypeptide 2 in 6.0 mg/kg and the high dose group of polypeptide 2 in 12.0 mg/kg (P<0.01); and the effect of anti-arterial thrombosis in the medium dose group of polypeptide 2 was better than that of the bivalirudin group.

TABLE 15

Effect of single intravenous administration of polypeptide 2 on FeCl₃-induced femoral artery thrombosis in rabbits ($\bar{x} \pm s$)

| Group | Dose (mg/kg) | n | Thrombus dry weight (mg) | Thrombus inhibitory rate (%) |
|---|---|---|---|---|
| Physiological saline group | — | 8 | 2.9 ± 1.9 | — |
| Bivalirudin | 6.0 | 8 | 1.5 ± 0.9 * | 48.20 |

TABLE 15-continued

Effect of single intravenous administration of
polypeptide 2 on FeCl$_3$-induced femoral artery thrombosis
in rabbits ($\bar{x} \pm s$)

| Group | Dose (mg/kg) | n | Thrombus dry weight (mg) | Thrombus inhibitory rate (%) |
|---|---|---|---|---|
| Enoxaparin | 200 U | 7 | 1.5 ± 0.4 * | 48.26 |
| Polypeptide 2, low dose | 3.0 | 6 | 1.4 ± 0.5 * | 52.99 |
| Polypeptide 2, medium dose | 6.0 | 8 | 1.2 ± 0.7 ** | 56.90 |
| Polypeptide 2, high dose | 12.0 | 8 | 1.1 ± 0.9 ** | 60.82 |

Compared with the physiological saline group,
* P < 0.05,
** P < 0.01.

Figure 11:
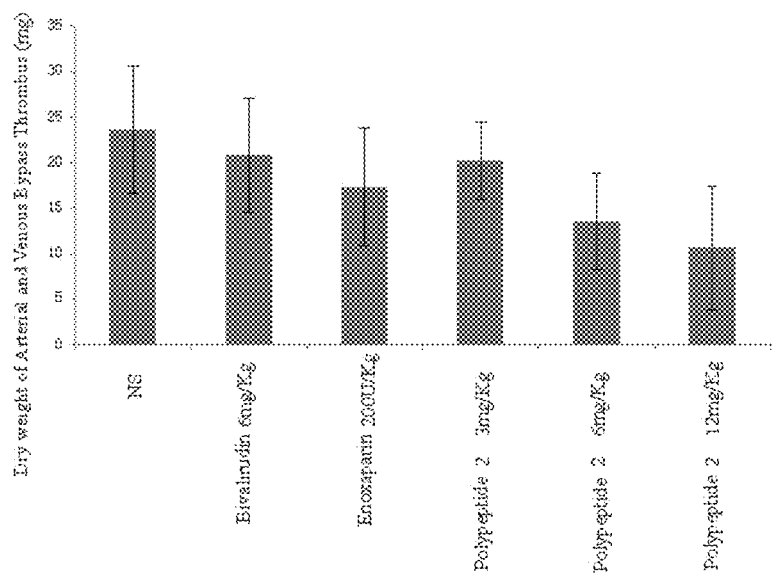
FIG. 11 shows effect of 15 minutes after single intravenous administration of polypeptide 2 on the dry weight of thrombus of femoral arterial and venous bypass thrombosis in rabbits.

4.2 Effect of Single Intravenous Administration of Polypeptide 2 on Femoral Arterial and Venous Bypass Thrombosis in Rabbits As shown in FIG. 11 and Table 16, single intravenous administration of different concentrations of polypeptide 2 can reduce the dry weight of thrombus in femoral arterial and venous bypass in rabbits and inhibit femoral and venous bypass thrombosis in rabbits. Compared with the physiological saline group, there was a very significant statistic difference for the medium dose group of polypeptide 2 in 6.0 mg/kg and the high dose group of polypeptide 2 in 12.0 mg/kg (P<0.01), and the effect of anti-arterial and venous bypass thrombosis in the medium dose group of polypeptide 2 was significantly better than that in the bivalirudin and enoxaparin groups.

TABLE 16

Effect of single intravenous administration of polypeptide 2 for 15 min on
femoral arterial and venous bypass thrombosis in rabbits ($\bar{x} \pm s$)

| Group | Dose (mg/kg) | n | Thrombus dry weight (mg) | Thrombus inhibitory rate (%) |
|---|---|---|---|---|
| Physiological saline group | — | 8 | 23.6 ± 7.0 | — |
| Bivalirudin | 6.0 | 8 | 20.8 ± 6.3 | 11.86 |
| Enoxaparin | 200 U | 7 | 17.3 ± 6.5 | 26.88 |
| Polypeptide 2, low dose | 3.0 | 6 | 20.2 ± 4.3 | 14.48 |
| Polypeptide 2, medium dose | 6.0 | 8 | 13.5 ± 5.3 ** | 42.80 |
| Polypeptide 2, high dose | 12.0 | 8 | 10.6 ± 6.8 ** | 55.24 |

Compared with the physiological saline group,
*P < 0.05,
** P < 0.01.

Figure 12:
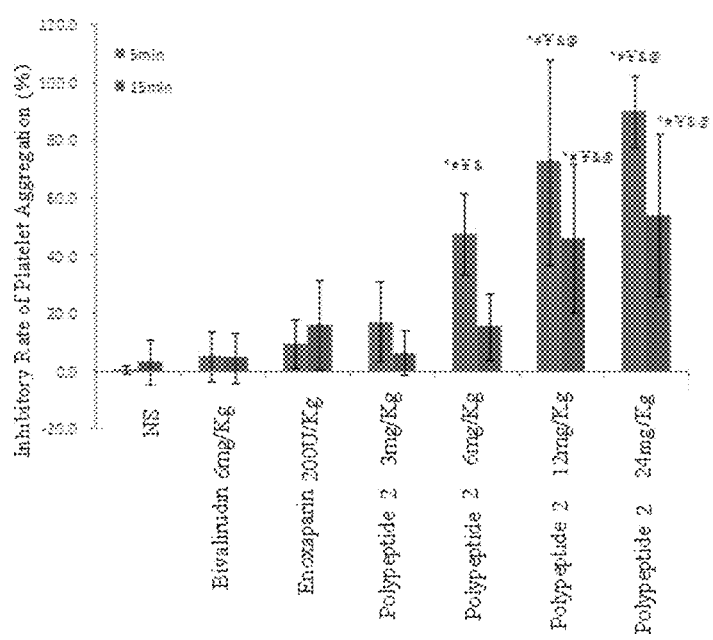
FIG. 12 shows effect of single intravenous administration of polypeptide 2 on platelet aggregation in rabbits (an inhibitory rate of platelet aggregation).

4.3 Effect of Single Intravenous Administration of Polypeptide 2 on Platelet Aggregation Function in Rabbits The results are shown in FIG. 12 and Table 17, which indicates that single intravenous administration of polypeptide 2 in each dose group can inhibit platelet aggregation in rabbits. After the administration was terminated, the inhibition on platelet aggregation was gradually weakened over time.

The single intravenous administration of polypeptide 2 in each dose group for 5 min can inhibit platelet aggregation in rabbits to different extents. Compared with the physiological saline group, there was a significant statistic difference for the medium dose group of polypeptide 2 in 6.0 mg/kg and the high dose group of polypeptide 2 in 12.0 mg/kg (P<0.05); and the antiplatelet effect in the medium dose group of polypeptide 2 was significantly better than that in the bivalirudin and enoxaparin groups. For the point of administration for 15 min, the inhibition on platelet aggregation in rabbits was gradually weakened. Compared with the physiological saline group, there was a significant difference for the high dose group of polypeptide 2 in 12.0 mg/kg (P<0.05).

TABLE 17

Effect of single intravenous administration of polypeptide 2 on platelet aggregation
function in rabbits (inhibitory rate of platelet aggregation, %, $\bar{x} \pm s$)

| Group | Dose (mg/kg) | n | Administration for 5 min | Administration for 15 min |
|---|---|---|---|---|
| Physiological saline | — | 8 | 0.6 ± 5.8 | 3.2 ± 6.0 |
| Bivalirudin | 6.0 | 8 | 5.2 ± 5.8 | 4.6 ± 6.0 |

TABLE 17-continued

Effect of single intravenous administration of polypeptide 2 on platelet aggregation function in rabbits (inhibitory rate of platelet aggregation, %, x̄ ± s)

| Group | Dose (mg/kg) | n | Administration for 5 min | Administration for 15 min |
|---|---|---|---|---|
| Enoxaparin | 200 | 7 | 9.5 ± 6.2 | 16.1 ± 6.5 |
| Polypeptide 2, low dose | 3.0 | 6 | 17.2 ± 6.7 | 6.3 ± 7.0 |
| Polypeptide 2, medium dose | 6.0 | 8 | 47.5 ± 5.8*#¥& | 15.4 ± 6.0 |
| Polypeptide 2, high dose | 12.0 | 7 | 72.5 ± 6.2*#¥&@ | 46.0 ± 6.5*#¥&@ |

Compared with the physiological saline group,
*P < 0.05; compared with the bivalirudin group,
P < 0.05; compared with enoxaparin group,
¥P < 0.05; compared with the low dose group of polypeptide 2,
&P < 0.05; compared with the medium dose group of polypeptide 2,
@p < 0.05

4.4 Effect of Single Intravenous Administration of Polypeptide 2 on Blood Coagulation Function in Rabbits The results show that, the administration of polypeptide 2 can prolong APTT, PT, TT and ACT in rabbits. After the administration was terminated, the prolongation of the above blood coagulation indicators was gradually weakened over time.

4.4.1 Effect on APTT in Rabbits

Figure 13:
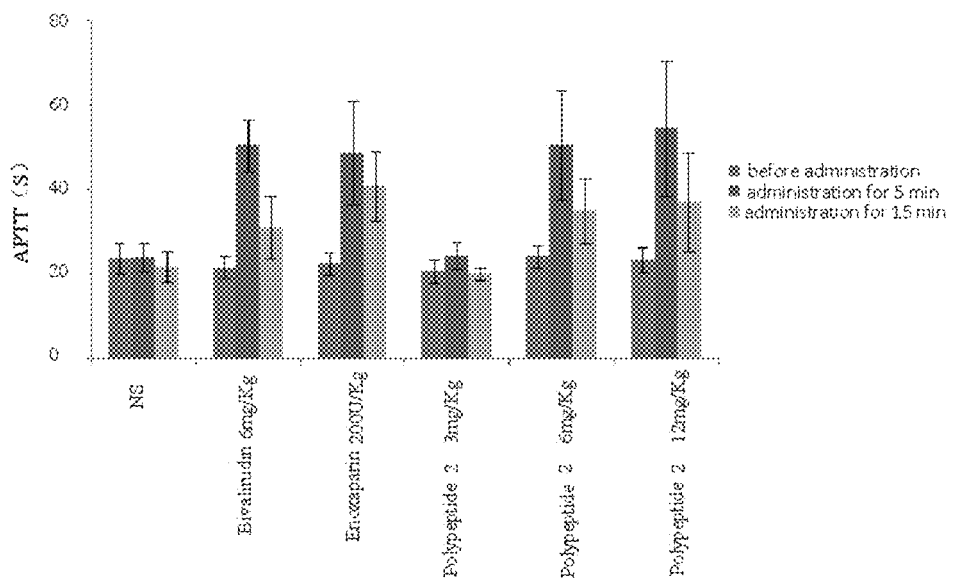
FIG. 13 shows effect of single intravenous administration of polypeptide 2 on APTT in rabbits.

The results are shown in FIG. 13 and Tables 18 and 19. In each dose group of polypeptide 2, the APTT in rabbits can be prolonged to different extents. The prolongation of APTT was gradually weakened over time within 15 min. After administration for 5 min, compared with the physiological saline group, there was a significant statistic difference for the medium dose group of polypeptide 2 in 6.0 mg/kg and the high dose group of polypeptide 2 in 12.0 mg/kg (P<0.05); and after administration for 15 min. compared with the physiological saline group, there was a significant statistic difference for the medium dose group of polypeptide 2 in 6.0 mg/kg and the high dose group of polypeptide 2 in 12.0 mg/kg (P<0.05).

TABLE 18

Effect of single intravenous administration of polypeptide 2 on APTT in rabbits (s, x ± Se)

| Group | Dose (mg/kg) | n | Before administration | Administration for 5 min | Administration for 15 min |
|---|---|---|---|---|---|
| Physiological saline | — | 8 | 23.5 ± 1.0 | 23.9 ± 3.6 | 21.8 ± 2.7 |
| Bivalirudin | 6.0 | 8 | 21.6 ± 1.0 | 50.4 ± 3.6* | 30.9 ± 2.7 |
| Enoxaparin | 200 | 7 | 22.5 ± 1.1 | 48.7 ± 3.9* | 40.9 ± 2.9* |
| Polypeptide 2, low dose | 3.0 | 6 | 20.6 ± 1.2 | 24.4 ± 4.2*¥ | 20.0 ± 3.1# |
| Polypeptide 2, medium dose | 6.0 | 8 | 24.1 ± 1.0 | 50.5 ± 3.6*& | 34.9 ± 2.7*& |
| Polypeptide 2, high dose | 12.0 | 8 | 23.3 ± 1.0 | 54.4 ± 3.6*& | 37.0 ± 2.7*& |

Compared with the physiological saline group,
*P < 0.05; compared with the bivalirudin group,
P < 0.05; compared with the enoxaparin group,
¥P < 0.05; compared with the low dose group of polypeptide 2,
&P < 0.05.

TABLE 19

Effect of single intravenous administration of polypeptide 2 on APTT in rabbits (fold of prolongation, x̄ ± s)

| Group | Dose (mg/kg) | n | Administration 5 min | Administration 15 min |
|---|---|---|---|---|
| Physiological saline | — | 8 | — | — |
| Bivalirudin | 6.0 | 8 | 2.4 ± 0.3 | 1.4 ± 0.3 |

TABLE 19-continued

Effect of single intravenous administration of polypeptide 2 on APTT in rabbits (fold of prolongation, x̄ ± s)

| Group | Dose (mg/kg) | n | Administration 5 min | Administration 15 min |
|---|---|---|---|---|
| Enoxaparin | 200 | 7 | 2.2 ± 0.5 | 1.8 ± 0.3 |
| Polypeptide 2, low dose | 3.0 | 6 | 1.2 ± 0.2 | 1.0 ± 0.1 |
| Polypeptide 2, medium dose | 6.0 | 8 | 2.1 ± 0.6 | 1.5 ± 0.4 |
| Polypeptide 2, high dose | 12.0 | 8 | 2.3 ± 0.6 | 1.6 ± 0.5 |

4.4.2 Effect on PT in Rabbits

Figure 14:
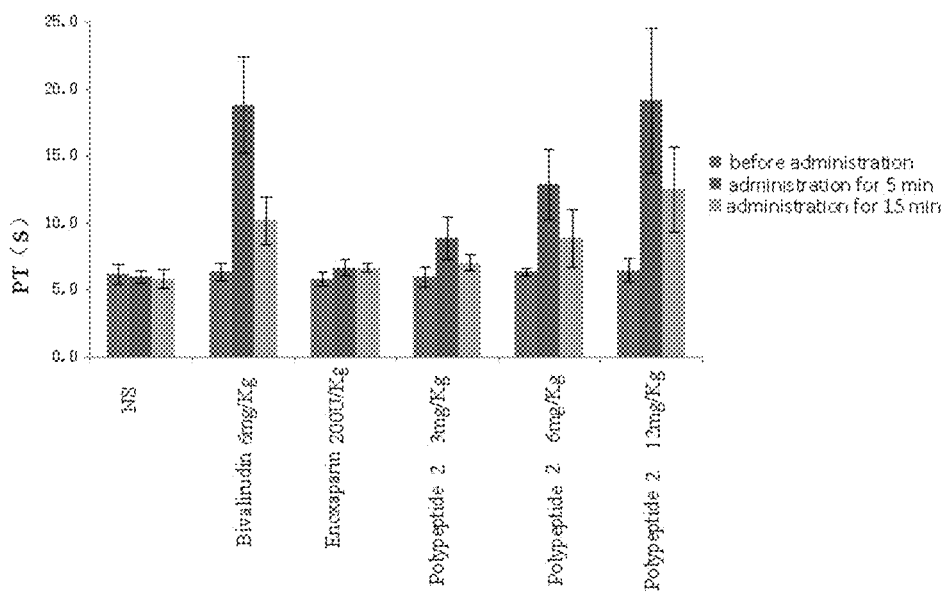
FIG. 14 shows effect of single intravenous administration of polypeptide 2 on PT in rabbits.

The results are shown in FIG. 14, Table 20 and Table 21. Polypeptide 2 in each dose group can prolong the PT in rabbits to different extents, and the prolongation of PT was gradually weakened over time within 15 min.

After administration for 5 min. compared with the physiological saline group, there was a significant statistic difference for the medium dose group of polypeptide 2 in 6.0 mg/kg and the high dose group of polypeptide 2 in 12.0 mg/kg (P<0.05); and after administration for 15 min, compared with the physiological saline group, there was a significant statistic difference for the medium dose group of polypeptide 2 in 6.0 mg/kg and the high dose group of polypeptide 2 in 12.0 mg/kg (P<0.05).

TABLE 20

Effect of single intravenous administration of polypeptide 2 on PT in rabbits (S, x ± Se)

| Group | Dose (mg/kg) | n | Before administration | Administration for 5 min | Administration for 15 min |
| --- | --- | --- | --- | --- | --- |
| Physiological saline | — | 8 | 6.2 ± 0.2 | 6.0 ± 1.1 | 5.8 ± 0.7 |
| Bivalirudin | 6.0 | 8 | 6.4 ± 0.2 | 18.8 ± 1.1 * | 10.2 ± 0.7 * |
| Enoxaparin | 200 | 7 | 5.8 ± 0.2 | 6.7 ± 1.1 # | 6.7 ± 0.8# |
| Polypeptide 2, low dose | 3.0 | 6 | 6.0 ± 0.3 | 8.9 ± 1.2# | 7.0 ± 0.8 |
| Polypeptide 2, medium dose | 6.0 | 8 | 6.3 ± 0.2 | 12.9 ± 1.1*#¥ | 8.9 ± 0.7 * |
| Polypeptide 2, high dose | 12.0 | 8 | 6.5 ± 0.2 | 19.2 ± 1.1 *¥& | 12.5 ± 0.7 *¥&@ |

TABLE 21

Effect of single intravenous administration of polypeptide 2 on PT in rabbits (fold of prolongation, $\bar{x}$ ± s)

| Group | Dose (mg/kg) | n | Administration 5 min | Administration 15 min |
| --- | --- | --- | --- | --- |
| Physiological saline | — | 8 | — | — |
| Bivalirudin | 6.0 | 8 | 3.0 ± 0.5 | 1.6 ± 0.2 |
| Enoxaparin | 200 | 7 | 1.2 ± 0.1 | 1.2 ± 0.1 |
| Polypeptide 2, low dose | 3.0 | 6 | 1.5 ± 0.4 | 1.2 ± 0.2 |
| Polypeptide 2, medium dose | 6.0 | 8 | 2.0 ± 0.4 | 1.4 ± 0.3 |
| Polypeptide 2, high dose | 12.0 | 8 | 3.0 ± 0.8 | 2.0 ± 0.6 |

4.4.3 Effect on TT in Rabbits

The results are shown in Table 22. Administration for 5 min and 15 min in each dose group of polypeptide 2 can prolong TT in rabbits, which is longer than the detection limit by 180 seconds.

TABLE 22

Effect of single intravenous administration of polypeptide 2 on TT in rabbits (S, x ± Se)

| Group | Dose (mg/kg) | n | Before administration | Administration for 5 min | Administration for 15 min |
| --- | --- | --- | --- | --- | --- |
| Physiological saline | — | 8 | 21.2 ± 0.8 | 20.3 ± 0.8 | 19.1 ± 0.7 |
| Bivalirudin | 6.0 | 8 | 22.4 ± 5.2 | >180 s | >180 s |
| Enoxaparin | 200 | 7 | 20.7 ± 4.2 | >180 s | >180 s |
| Polypeptide 2, low dose | 3.0 | 6 | 21.0 ± 2.6 | >180 s | >180 s |
| Polypeptide 2, medium dose | 6.0 | 8 | 22.3 ± 1.9 | >180 s | >180 s |
| Polypeptide 2, high dose | 12.0 | 8 | 21.8 ± 6.4 | >180 s | >180 s |

4.4.4 Effect of Polypeptide 2 on ACT in Rabbits

Figure 15:
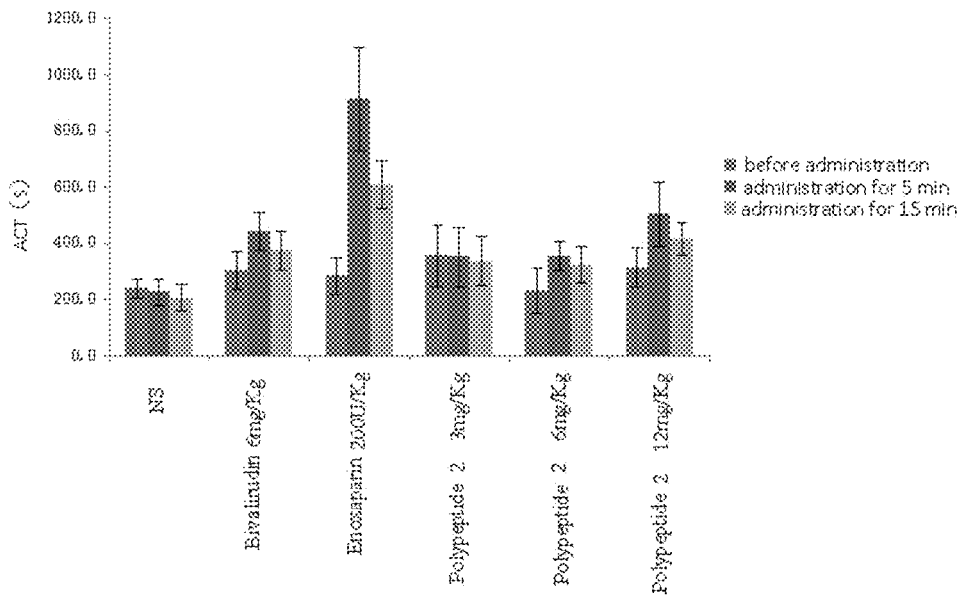
FIG. 15 shows effect of single intravenous administration of polypeptide 2 on ACT in rabbits.

The results are shown in FIG. 15, Table 23 and Table 24. Polypeptide 2 in each dose group can prolong the ACT in rabbits to different extents, and the prolongation of ACT was gradually weakened over time within 15 min.

After administration for 5 min, compared with the physiological saline group, there was a significant statistic difference for the high dose group of polypeptide 2 in 12.0 mg/kg ($P<0.05$).

After administration for 15 min, compared with the physiological saline group, there was a significant statistic difference for the low dose group in 3.0 mg/kg, the medium dose group in 6.0 mg/kg and the high dose group in 12.0 mg/kg of polypeptide 2 ($P<0.05$).

TABLE 23

Effect of single intravenous administration of polypeptide 2 on ACT in rabbits (s, x ± Se)

| Group | Dose (mg/kg) | n | Before administration | Administration for 5 min | Administration for 15 min |
| --- | --- | --- | --- | --- | --- |
| Physiological saline | — | 8 | 240.0 ± 24.0 | 226.9 ± 35.3 | 208.1 ± 24.1 |
| Bivalirudin | 6.0 | 8 | 305.6 ± 24.0 | 443.8 ± 35.3* | 375.0 ± 24.1* |

TABLE 23-continued

Effect of single intravenous administration of polypeptide 2 on ACT in rabbits (s, x ± Se)

| Group | Dose (mg/kg) | n | Before administration | Administration for 5 min | Administration for 15 min |
|---|---|---|---|---|---|
| Enoxaparin | 200 | 7 | 285.0 ± 25.6 | 915.0 ± 37.7*# | 610.7 ± 25.7*# |
| Polypeptide 2, low dose | 3.0 | 6 | 357.5 ± 27.7 | 352.5 ± 40.7$^¥$ | 337.5 ± 27.8*$^¥$ |
| Polypeptide 2, medium dose | 6.0 | 8 | 232.5 ± 24.0 | 356.3 ± 35.3$^¥$ | 324.4 ± 24.1*$^¥$ |
| Polypeptide 2, high dose | 12.0 | 8 | 315.0 ± 24.0 | 505.6 ± 35.3*$^{¥\&@}$ | 418.1 ± 24.1*$^¥$ |

Compared with the physiological saline group,
*P < 0.05; compared with the bivalirudin group,
P < 0.05; compared with the enoxaparin group,
¥P < 0.05; compared with the low dose group of polypeptide 2,
&P < 0.05; compared with the medium dose group of polypeptide 2,
@P < 0.05

TABLE 24

Effect of single intravenous administration of polypeptide 2 on ACT in rabbits (fold of prolongation, x̄ ± s)

| Group | Dose (mg/kg) | n | After administration 5 min | After administration 15 min |
|---|---|---|---|---|
| Physiological saline | — | — | — | — |
| Bivalirudin | 6.0 | 8 | 1.5 ± 0.3 | 1.3 ± 0.4 |
| Enoxaparin | 200 | 7 | 3.4 ± 1.1 | 2.2 ± 0.7 |
| Polypeptide 2, low dose | 3.0 | 6 | 1.0 ± 0.2 | 1.0 ± 0.1 |
| Polypeptide 2, medium dose | 6.0 | 8 | 1.7 ± 0.7 | 1.6 ± 0.9 |
| Polypeptide 2, high dose | 12.0 | 8 | 1.7 ± 0.6 | 1.4 ± 0.3 |

The single intravenous administration of polypeptide 2 can inhibit $FeCl_3$-induced femoral arterial thrombosis in rabbits and dose-dependently inhibit femoral arterial and venous bypass thrombosis in rabbits, in which the antithrombotic effect in the medium and high doe groups thereof is superior to that in the bivalirudin group; as well as polypeptide 2 can inhibit platelet aggregation in rabbits in a dose-dependent manner, affect the blood coagulation function in rabbits and prolong APTT, PT, TT and ACT.

Test Example 8

This test example is used to demonstrate the protective effect of polypeptide 2 on progressive ischemic stroke.

1. Experimental animals: 60 healthy adult male SD rats, with body weight of 250 g to 300 g, purchased from Animal Center of Xi'an Jiaotong University Medical College. Animal production license number: SCXK (shaanxi) 2012-003.

2. Samples to be tested: polypeptide 2 having a peptide content of 97.21%; control drug: enoxaparin injection, produced by Sanofi (Beijing) Pharmaceutical Co., Ltd., Lot number: 4SH69.

3. Experimental Method:

3.1 Formulation of Solution: Polypeptide 2: A Stock Solution of 2 mg/ml was Formulated Prior to Use.

3.2 Grouping and administration: At 15 min after the mold was established, administration was started by jugular vein intubation, with the first dose and the maintenance dose for 60 min, in which the administration group was administered with polypeptide 2 at a dose of 0.25 mg/kg+0.75 mg/kg/h, while the model group was administered with physiological saline.

3.3 Experimental operation: Suture method (common carotid artery insertion method): the skin on the neck was cut open from a median incision thereon, and the common, external and internal carotid arteries were isolated therefrom. The common carotid artery was ligated at the heart-proximal end and the external carotid artery was ligated at the distal end. The distal end of the internal carotid artery was temporarily occluded with a small vascular clamp, and at the bifurcation of the common, external and internal carotid arteries, a thread for ligature was reserved. A small opening was cut with an eye scissor on the common carotid artery which was close to the internal carotid artery, to allow a certain degree of bending of the MCAO thread, which inserted into the internal carotid artery along the common carotid artery. During the thread insertion, the thread bended towards the direction of the operator, which was slowly pushed forward about 18 mm (from the bifurcation of the arteries), and terminated when a resistance was felt. The reserved thread was ligated at the bifurcation to fix the thread. At 15 min after the mold was established, the first dose was administered followed by maintenance dose for 60 min, and after the administration was finished, the wound in the neck was sutured in a conventional manner.

4. Test Indicators 4.1 Neurobehavioral scores: Rats in both the groups were evaluated in terms of their neurobehavioral scores at 4, 8, and 24 hours after the surgery, with a Longa five-point quartering method as the standard: 0 point: no neurological defect; 1 point: adduction and failure to full extension of forelimbs on contralateral side when tail lifting; 2 points: rotation to the contralateral side; 3 points: toppling and falling to the contralateral side when walking; 4 points: failure to walk or coma. Cases with 1 to 4 points were classified as valid models.

4.2 observing infarct lesions and infarct volume by TTC staining: At 24 hours after the surgery, the animals were sacrificed and the brain was taken for TTC staining. The infarct volume was calculated by using a mapping software.

4.3 Cerebral index, cerebral water content: The rats in each group were rapidly decapitated 24 hours after the surgery and model establishment, and the whole brain was rapidly peeled off, which was then weighed for wet weight and used to calculate the brain index: Brain index=Brain wet weight/Body weight*100%

5. Test Results

The test results in Tables 25 and 26 show that, polypeptide 2 at the doses of 0.5+1.25 and 1.0+2.5 (mg/kg+mg/kg/h) reduced the cerebral infarct volume from (23.41±10.08)% to (11.12±6.56)% and (8.01±6.66)% 24 hours after the surgery, respectively; and the neurobehavioral injury was also improved, indicating the protective effect on the experimental cerebral infarction.

TABLE 25

Effect of polypeptide 2 on neurological behaviors (x ± s)

| Group | Dose (mg/kg + mg/kg/h) | n | 4 h | 8 h | 24 h |
|---|---|---|---|---|---|
| Sham operation group | — | 5 | 0 | 0 | 0 |
| Model group | — | 19 | 2.32 ± 0.75 | 2.37 ± 0.83 | 2.50 ± 0.99 |
| Enoxaparin group | 90 U/kg + 120 U/kg/h | 8 | 0.63 ± 0.74** | 0.88 ± 0.64** | 1.38 ± 0.74* |
| Polypeptide 2 group 1 | 0.5 + 1.25 | 7 | 1.00 ± 0.58** | 1.00 ± 0.58** | 1.00 ± 0.58** |
| Polypeptide 2 group 2 | 1.0 + 2.5 | 7 | 0.86 ± 1.07** | 0.86 ± 0.90** | 1.14 ± 0.69** |

Compared with the model group,
*$P < 0.05$,
**$P < 0.01$

TABLE 26

Effect of polypeptide 2 on cerebral infarct volume and cerebral index (x ± s)

| Group | Dose (mg/kg + mg/kg/h) | n | Cerebral infarct volume ratio (%) | Cerebral index (%) |
|---|---|---|---|---|
| Sham operation group | — | 5 | 0 ± 0 | 0.6175 ± 0.0511** |
| Model group | — | 19 | 23.41 ± 10.08 | 0.7167 ± 0.0555 |
| Enoxaparin group | 90 U/kg + 120 U/kg/h | 8 | 10.22 ± 5.38** | 0.6819 ± 0.0356 |
| Polypeptide 2 group 1 | 0.5 + 1.25 | 7 | 11.12 ± 6.56** | 0.6648 ± 0.0374* |
| Polypeptide 2 group 2 | 1.0 + 2.5 | 7 | 8.01 ± 6.66** | 0.6830 ± 0.0322 |

Compared with the model group,
*$P < 0.05$,
**$P < 0.01$

Test Example 9

This test example is used to demonstrate the protective effect of polypeptide 2 on thrombin-induced pulmonary embolism in mice.

1. Experimental animals: Kunming mice, male, 6 to 8 weeks old, 20 g to 25 g, provided by experimental animal center of Xi'an Jiaotong University. Animal production license number SCXK (Shaanxi) 2012-003.

2. Experimental Reagents 2.1 Thrombin: sigma Company. Lot number T4648, derived from bovine serum, specification: 1000 U/bottle.

2.2 Enoxaparin injection: 0.4 ml: 4000AxaIU, Sanofi (Beijing) Pharmaceutical Co., Ltd., Subpackaging Approval Number: State Medicine Approval No: J20090094.

2.3 Polypeptide 2, which was obtained by entrusting Jill Biochemical (Shanghai) Co., Ltd., Lot number P131029-ML360794, having a peptide content of 97.21%.

3. Experimental Equipment

BC-2800Vet Mindray automatic blood cell analyzer, Shenzhen Mindray Biomedical Electronics Co., Ltd.

4. Experimental Method

Mice were randomly divided into 7 groups with 10 mice per group, in which group 1 was physiological saline group, group 2 was model control group, group 3 was positive control group of enoxaparin 0.5 mg/kg, group 4 was positive control group of bivalirudin 8 mg/kg, group 5 was low dose group of polypeptide 2 at 2.5 mg/kg, group 6 was medium dose group of polypeptide 2 at 5.0 mg/kg, and group 7 was high dose group of polypeptide 2 at 10.0 mg/kg. Except that physiological saline group and model control group were subjected to tail intravenous injection of 200 μl physiological saline, the other groups were given according to the doses, respectively. After 2 min, the mice in physiological saline group were administered with 100 μl physiological saline through tail intravenous injection and the other groups were each administered with 100 μl thrombin based on 1500 u/kg (80% to 90% of the lethal dose) through tail intravenous injection. The mice were observed after the administration for their death within 15 min. Mice those did not die within 15 min were subjected to the treatments as follows.

(1) Recording mortality rate: the death status of mice with acute pulmonary embolism mice within 15 min was recorded and the survival time was recorded, to calculate the mortality rate;

(2) Determining lung coefficient: immediately after death, the bronchial and adipose tissues were dissected away from the lung tissue, and the lung tissue was washed with distilled water, and weighed for the lung weight after soaking up the water on the surface of the lung with a filter paper. The lung was taken out and weighed, to calculate the lung coefficient. Lung coefficient=Lung weight/Body weight×100%;

(3) Determining the number of platelets: for the mice that did not die within 15 min. blood was taken from eyes, and measured for its number of platelets after EDTA anticoagulation. The lung was immediately dissected and taken out and weighed to determine the lung coefficient.

5. Experimental Results

In the LPS model group, 12 of 13 mice died with a mortality rate of 85%, which had a very significant difference from that of the physiological saline group (P<0.01). In the groups of enoxaparin 0.5 mg/kg, bivalirudin 8 mg/kg, and polypeptide 2 at a high dose 10.0 mg/kg, 1 of 10 mice died with a mortality rate of 10%, which have a very significant difference from that of the model group, respectively (P<0.01). In the medium dose group of polypeptide 2 at 5.0 mg/kg, 3 of 10 mice died with a mortality rate of 30%, which had a very significant difference from that of the model group (P<0.01). There was no significant difference in mortality between both the groups of polypeptide 2 and enoxaparin 0.5 mg/kg or bivalirudin 8 mg/kg, respectively (P>0.05).

Figure 16:
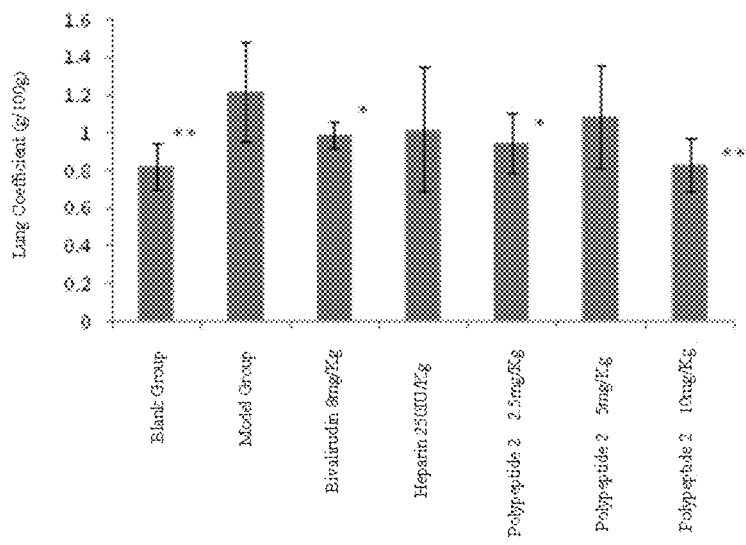
FIG. 16 shows effect of polypeptide 2 on the lung coefficient in a thrombin (1500 u/kg)-induced mouse pulmonary embolism model.

In the low dose group of polypeptide 2 at 2.5 mg/kg, 6 of 10 mice died with a mortality rate of 60%, which has no significant difference compared with that of the model group (P>0.05), had a significant difference compared with that of enoxaparin 250 U/kg and bivalirudin 8 mg/kg (P<0.01), and had a significant difference compared with that in groups of polypeptide 2 at a medium dose 5.0 mg/kg and at a high dose 10.0 mg/kg (P<0.05). For the mice in the model group, the lung coefficient significantly increased, which had a very significant difference (P<0.01) compared with the physiological saline group; the lung coefficient in the bivalirudin 8 mg/kg group decreased, which had a significant difference (P<0.05) compared with the model group; and the lung coefficient of mice in the high dose group of polypeptide 2 at 10.0 mg/kg group decreased, which had a very significant difference compared with the model group (P<0.01). The results are shown in Table 27 and FIG. 16, indicating that polypeptide 2 has protective effect on thrombin-induced pulmonary embolism in mice.

TABLE 27

Effect of polypeptide 2 on thrombin-induced pulmonary embolism in mice

| Group | Dose (mg/kg) | n | Mortality rate (%) | Lung coefficient (g/100 g) | Number of platelets ($\times 10^9$) |
|---|---|---|---|---|---|
| Blank control group | — | 10 | 0** | 0.82 ± 0.12** | 1069.4 ± 407.01 |
| Model group | — | 13 | 85 | 1.22 ± 0.26 | 65.45 ± 5.1 |
| Enoxaparin group | 250 IU/kg | 10 | 10**## | 1.02 ± 0.33 | 459.83 ± 49.66 |
| Bivalirudin group | 8.0 | 10 | 10**## | 0.99 ± 0.07* | 411.89 ± 175.52 |
| Polypeptide 2, high dose group | 10.0 | 10 | 10**# | 0.83 ± 0.14** | 529.57 ± 104.28 |
| Polypeptide 2, medium dose group | 5.0 | 10 | 30**# | 1.08 ± 0.27 | 207.83 ± 33.09 |
| Polypeptide 2, low dose group | 2.5 | 10 | 60 | 0.94 ± 0.16* | 165.33 ± 20.2 |

Compared with the model group,
*P < 0.05,
**P < 0.01; compared with the low dose group of polypeptide 2:
P < 0.05,
P < 0.01.

While the invention has been described in detail by way of the general description and the above specific embodiments, it will be apparent for those skilled in the art that certain modifications or improvements may be made thereto on the basis of the invention. Therefore, these modifications or improvements made without departing from the spirit of the present disclosure all fall within the protection scope of the present invention.

INDUSTRIAL APPLICABILITY

The multi-target antagonistic compound with anticoagulation and platelet GPIIb/IIIa receptor antagonism of the invention has direct, reversible and specific anti-thrombin function and also has function of inhibiting the GPIIb/IIIa receptors, which can achieve the anticoagulant and anti-thrombotic effect at a low dose. At the same time, the bleeding risk is reduced, and problems such as dose matching, bleeding, coordination caused by drug combination are avoided.

What is claimed is:

1. A multi-target compound with anticoagulation and platelet GPIIb/IIIa receptor antagonism, said compound having a structure as shown in Formula (1):

A-L-B-L'-C    Formula (1)

wherein A and B are thrombin binding sites, C is a platelet GPIIb/IIIa receptor binding site, L is a first linker, and L' is a second linker;
wherein L' has a structure as shown in Formula (2):

$((Gly)_{n_1}\text{-}(Ser)_{n_2})$    Formula (2)

wherein n1 is 1, 2, 3 or 4; n2 is 0 or 1; and n3 is 0, 1, 2 or 3; or
L' has a structure as shown in Formula (3):

$(Glu\text{-}Ala\text{-}Ala\text{-}Ala\text{-}Lys)_{n_1}$    Formula (3)

wherein n1 is 0, 1, 2 or 3; or
L' has a structure as shown in Formula (4):

$(Arg\text{-}Val\text{-}Leu\text{-}Ala\text{-}Glu\text{-}Ala)_{n_1}$    Formula (4)

wherein n1 is 0, 1, 2 or 3;
wherein C has a structure as shown in Formula (7):

Cys-Har-C1-Asp-Trp-Pro-C2    Formula (7)

wherein C1 is Gly or Ser; C2 is Cys or a structure obtained by replacing —OH in Cys with —$NH_2$; and a disulfide bond is formed between two mercapto groups in the Formula (7);
wherein A-L-B is selected from one of polypeptide sequences shown in SEQ ID NO: 1 to SEQ ID NO: 3.

2. The compound according to claim 1, wherein said compound has a structure as shown in Formula (9):

X-A-L-B-L'-C—Y    Formula (9)

wherein X is one selected from hydrogen, one or two C1-C6 alkyl, one or two C2-C10 acyl, benzyloxycarbonyl and tert-butoxycarbonyl; Y is one selected from OH, C1-C6 alkoxy, an amino, and an amino substituted with one or two C1-C4 alkyl.

3. The compound according to claim 2, wherein said compound comprises a polypeptide sequence of polypeptide structures shown in SEQ ID NO: 4 to SEQ ID NO: 7.

4. The compound according to claim 3, wherein said compound is selected from one of polypeptide structures shown in SEQ ID NO: 4 to SEQ ID NO: 7.

5. A salt of a compound according to claim 1.

6. The salt of a compound according to claim 5, wherein said salt is an acetate salt of the compound or a trifluoroacetate salt of the compound.

7. A method for preparing a compound according to claim 1, wherein said method comprises the steps of:
(1) sequentially introducing protected amino acids or fragments starting from carboxyl terminal according to polypeptide sequence using a solid phase synthesis method, to obtain a polypeptide-Wang resin in which side chains of amino acids are all protected;
(2) subjecting the polypeptide-Wang resin in which side chains of amino acids are all protected to acid hydrolysis with an acid hydrolyzing agent to obtain a crude linear polypeptide; and
(3) cyclizing the crude linear polypeptide to form a disulfide bond and then purifying with high-pressure preparative liquid chromatography, to obtain a polypeptide sequence.

8. A pharmaceutical composition, wherein said pharmaceutical composition comprises a compound according to claim 1 as an active ingredient.

9. The pharmaceutical composition according to claim 8, wherein the dosage form of said pharmaceutical composition is an injection, a tablet, a capsule, a pill, a powder, a granule, a suspension or an emulsion.

10. A pharmaceutical composition, wherein said pharmaceutical composition comprises a salt according to claim 5 as an active ingredient.

11. The pharmaceutical composition according to claim 10, wherein the dosage form of said pharmaceutical composition is an injection, a tablet, a capsule, a pill, a powder, a granule, a suspension or an emulsion.

12. A method of treating the following diseases or conditions:
peripheral arterial thrombosis; arterial and venous bypass thrombosis; thrombosis formed in acute coronary syndromes, percutaneous coronary intervention, or therapy with a coronary stent in PCI; progressive ischemic stroke; acute pulmonary embolism; or thrombosis in organ and tissue transplantation;
comprising administering a subject in need thereof a compound according to claim 1.

13. A method of treating the following diseases or conditions:
peripheral arterial thrombosis; arterial and venous bypass thrombosis; thrombosis formed in acute coronary syndromes, percutaneous coronary intervention, or therapy with a coronary stent in PCI; progressive ischemic stroke; acute pulmonary embolism; or thrombosis in organ and tissue transplantation;
comprising administering to a subject in need thereof a salt according to claim 5.

\* \* \* \* \*

SEQUENCE LISTING

<160> NUMBER OF SEQ ID NOS: 27

<210> SEQ ID NO 1
<211> LENGTH: 20
<212> TYPE: PRT
<213> ORGANISM: Artificial sequence
<220> FEATURE:
<223> OTHER INFORMATION: The N-terminal phenylalanine is D-phenylalanine

<400> SEQUENCE: 1

Phe Pro Arg Pro Gly Gly Gly Gly Asn Gly Asp Tyr Glu Asp Ile Pro
1               5                   10                  15

Glu Glu Tyr Leu
            20

```
<210> SEQ ID NO 2
<211> LENGTH: 20
<212> TYPE: PRT
<213> ORGANISM: Artificial sequence
<220> FEATURE:
<223> OTHER INFORMATION: The N-terminal phenylalanine is D-phenylalanine

<400> SEQUENCE: 2

Phe Pro Arg Ser Gly Gly Gly Gly Asn Gly Asp Phe Glu Asp Ile Pro
1               5                   10                  15

Glu Glu Tyr Leu
            20

<210> SEQ ID NO 3
<211> LENGTH: 20
<212> TYPE: PRT
<213> ORGANISM: artificial sequence
<220> FEATURE:
<223> OTHER INFORMATION: The N-terminal phenylalanine is D-phenylalanine

<400> SEQUENCE: 3

Phe Pro Arg Pro Gly Gly Gly Gly Asn Gly Asp Phe Glu Glu Ile Pro
1               5                   10                  15

Glu Glu Tyr Leu
            20

<210> SEQ ID NO 4
<211> LENGTH: 32
<212> TYPE: PRT
<213> ORGANISM: artificial sequence
<220> FEATURE:
<223> OTHER INFORMATION: The N-terminal phenylalanine is D-phenylalanine
<220> FEATURE:
<223> OTHER INFORMATION: a disulfide bond is formed between two Cys
<220> FEATURE:
<221> NAME/KEY: MISC_FEATURE
<222> LOCATION: (27)..(27)
<223> OTHER INFORMATION: Xaa is homoarginine

<400> SEQUENCE: 4

Phe Pro Arg Pro Gly Gly Gly Gly Asn Gly Asp Phe Glu Glu Ile Pro
1               5                   10                  15

Glu Glu Tyr Leu Gly Gly Gly Gly Ser Cys Xaa Gly Asp Trp Pro Cys
            20                  25                  30

<210> SEQ ID NO 5
<211> LENGTH: 32
<212> TYPE: PRT
<213> ORGANISM: artificial sequence
<220> FEATURE:
<223> OTHER INFORMATION: The N-terminal phenylalanine is D-phenylalanine
<220> FEATURE:
<223> OTHER INFORMATION: a disulfide bond is formed between two Cys
<220> FEATURE:
<221> NAME/KEY: MISC_FEATURE
<222> LOCATION: (27)..(27)
<223> OTHER INFORMATION: Xaa is homoarginine

<400> SEQUENCE: 5

Phe Pro Arg Pro Gly Gly Gly Gly Asn Gly Arg Phe Glu Glu Ile Pro
1               5                   10                  15

Glu Glu Tyr Leu Glu Ala Ala Ala Lys Cys Xaa Gly Asp Trp Pro Cys
            20                  25                  30

<210> SEQ ID NO 6
<211> LENGTH: 27
<212> TYPE: PRT
```

```
<213> ORGANISM: artificial sequence
<220> FEATURE:
<223> OTHER INFORMATION: The N-terminal phenylalanine is D-phenylalanine
<220> FEATURE:
<223> OTHER INFORMATION: a disulfide bond is formed between two Cys
<220> FEATURE:
<221> NAME/KEY: MISC_FEATURE
<222> LOCATION: (22)..(22)
<223> OTHER INFORMATION: Xaa is homoarginine

<400> SEQUENCE: 6

Phe Pro Arg Pro Gly Gly Gly Gly Asn Gly Asp Phe Glu Glu Ile Pro
1               5                   10                  15
Glu Glu Tyr Leu Cys Xaa Gly Asp Trp Pro Cys
            20                  25

<210> SEQ ID NO 7
<211> LENGTH: 33
<212> TYPE: PRT
<213> ORGANISM: artificial sequence
<220> FEATURE:
<223> OTHER INFORMATION: The N-terminal phenylalanine is D-phenylalanine
<220> FEATURE:
<223> OTHER INFORMATION: a disulfide bond is formed between two Cys
<220> FEATURE:
<221> NAME/KEY: MISC_FEATURE
<222> LOCATION: (28)..(28)
<223> OTHER INFORMATION: Xaa is homoarginine

<400> SEQUENCE: 7

Phe Pro Arg Pro Gly Gly Gly Gly Asn Gly Asp Phe Glu Glu Ile Pro
1               5                   10                  15
Glu Glu Tyr Leu Arg Val Leu Ala Glu Ala Cys Xaa Gly Asp Trp Pro
            20                  25                  30
Cys

<210> SEQ ID NO 8
<211> LENGTH: 5
<212> TYPE: PRT
<213> ORGANISM: artificial sequence
<220> FEATURE:
<223> OTHER INFORMATION: synthesized peptide

<400> SEQUENCE: 8

Gly Gly Gly Gly Ser
1               5

<210> SEQ ID NO 9
<211> LENGTH: 8
<212> TYPE: PRT
<213> ORGANISM: artificial sequence
<220> FEATURE:
<223> OTHER INFORMATION: synthesized peptide

<400> SEQUENCE: 9

Gly Gly Gly Ser Gly Gly Gly Ser
1               5

<210> SEQ ID NO 10
<211> LENGTH: 10
<212> TYPE: PRT
<213> ORGANISM: artificial sequence
<220> FEATURE:
<223> OTHER INFORMATION: synthesized peptide

<400> SEQUENCE: 10

Gly Gly Gly Gly Ser Gly Gly Gly Gly Ser
```

```
1               5               10
```

<210> SEQ ID NO 11
<211> LENGTH: 12
<212> TYPE: PRT
<213> ORGANISM: artificial sequence
<220> FEATURE:
<223> OTHER INFORMATION: synthesized peptide

<400> SEQUENCE: 11

```
Gly Gly Gly Ser Gly Gly Gly Ser Gly Gly Gly Ser
1               5                   10
```

<210> SEQ ID NO 12
<211> LENGTH: 15
<212> TYPE: PRT
<213> ORGANISM: artificial sequence
<220> FEATURE:
<223> OTHER INFORMATION: synthesized peptide

<400> SEQUENCE: 12

```
Gly Gly Gly Gly Ser Gly Gly Gly Gly Ser Gly Gly Gly Gly Ser
1               5                   10                  15
```

<210> SEQ ID NO 13
<211> LENGTH: 8
<212> TYPE: PRT
<213> ORGANISM: artificial sequence
<220> FEATURE:
<223> OTHER INFORMATION: synthesized peptide

<400> SEQUENCE: 13

```
Gly Gly Gly Gly Gly Gly Gly Gly
1               5
```

<210> SEQ ID NO 14
<211> LENGTH: 12
<212> TYPE: PRT
<213> ORGANISM: artificial sequence
<220> FEATURE:
<223> OTHER INFORMATION: synthesized peptide

<400> SEQUENCE: 14

```
Gly Gly Gly Gly Gly Gly Gly Gly Gly Gly Gly Gly
1               5                   10
```

<210> SEQ ID NO 15
<211> LENGTH: 5
<212> TYPE: PRT
<213> ORGANISM: artificial sequence
<220> FEATURE:
<223> OTHER INFORMATION: synthesized peptide

<400> SEQUENCE: 15

```
Glu Ala Ala Ala Lys
1               5
```

<210> SEQ ID NO 16
<211> LENGTH: 10
<212> TYPE: PRT
<213> ORGANISM: artificial sequence
<220> FEATURE:
<223> OTHER INFORMATION: synthesized peptide

<400> SEQUENCE: 16

```
Glu Ala Ala Ala Lys Glu Ala Ala Ala Lys
1               5                   10
```

-continued

```
<210> SEQ ID NO 17
<211> LENGTH: 15
<212> TYPE: PRT
<213> ORGANISM: artificial sequence
<220> FEATURE:
<223> OTHER INFORMATION: synthesized peptide

<400> SEQUENCE: 17

Glu Ala Ala Ala Lys Glu Ala Ala Ala Lys Glu Ala Ala Ala Lys
1               5                   10                  15

<210> SEQ ID NO 18
<211> LENGTH: 6
<212> TYPE: PRT
<213> ORGANISM: artificial sequence
<220> FEATURE:
<223> OTHER INFORMATION: synthesized peptide

<400> SEQUENCE: 18

Arg Val Leu Ala Glu Ala
1               5

<210> SEQ ID NO 19
<211> LENGTH: 12
<212> TYPE: PRT
<213> ORGANISM: artificial sequence
<220> FEATURE:
<223> OTHER INFORMATION: synthesized peptide

<400> SEQUENCE: 19

Arg Val Leu Ala Glu Ala Arg Val Leu Ala Glu Ala
1               5                   10

<210> SEQ ID NO 20
<211> LENGTH: 18
<212> TYPE: PRT
<213> ORGANISM: artificial sequence
<220> FEATURE:
<223> OTHER INFORMATION: synthesized peptide

<400> SEQUENCE: 20

Arg Val Leu Ala Glu Ala Arg Val Leu Ala Glu Ala Arg Val Leu
1               5                   10                  15

Ala Glu Ala

<210> SEQ ID NO 21
<211> LENGTH: 7
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (2)..(2)
<223> OTHER INFORMATION: Xaa is homoarginine

<400> SEQUENCE: 21

Cys Xaa Gly Asp Trp Pro Cys
1               5

<210> SEQ ID NO 22
<211> LENGTH: 7
<212> TYPE: PRT
<213> ORGANISM: artificial sequence
<220> FEATURE:
<223> OTHER INFORMATION: synthesized peptide
```

```
<220> FEATURE:
<221> NAME/KEY: MISC_FEATURE
<222> LOCATION: (2)..(2)
<223> OTHER INFORMATION: Xaa is homoarginine

<400> SEQUENCE: 22

Cys Xaa Ser Asp Trp Pro Cys
1               5

<210> SEQ ID NO 23
<211> LENGTH: 8
<212> TYPE: PRT
<213> ORGANISM: artificial sequence
<220> FEATURE:
<223> OTHER INFORMATION: synthesized peptide

<400> SEQUENCE: 23

Glu Glu Ile Pro Glu Glu Tyr Leu
1               5

<210> SEQ ID NO 24
<211> LENGTH: 7
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is Cys(Trt)
<220> FEATURE:
<221> NAME/KEY: MISC_FEATURE
<222> LOCATION: (2)..(2)
<223> OTHER INFORMATION: Xaa is homoarginine
<220> FEATURE:
<221> NAME/KEY: MISC_FEATURE
<222> LOCATION: (4)..(4)
<223> OTHER INFORMATION: Xaa is Asp(OtBu)
<220> FEATURE:
<221> NAME/KEY: MISC_FEATURE
<222> LOCATION: (7)..(7)
<223> OTHER INFORMATION: Xaa is Cys(Trt)

<400> SEQUENCE: 24

Xaa Xaa Gly Xaa Trp Pro Xaa
1               5

<210> SEQ ID NO 25
<211> LENGTH: 29
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (3)..(3)
<223> OTHER INFORMATION: Xaa is Arg(pbf)
<220> FEATURE:
<221> NAME/KEY: MISC_FEATURE
<222> LOCATION: (9)..(9)
<223> OTHER INFORMATION: Xaa is Asn(Trt)
<220> FEATURE:
<221> NAME/KEY: MISC_FEATURE
<222> LOCATION: (11)..(11)
<223> OTHER INFORMATION: Xaa is Asp(OtBu)
<220> FEATURE:
<221> NAME/KEY: MISC_FEATURE
<222> LOCATION: (14)..(14)
<223> OTHER INFORMATION: Xaa is Glu(OtBu)
<220> FEATURE:
<221> NAME/KEY: MISC_FEATURE
<222> LOCATION: (15)..(15)
<223> OTHER INFORMATION: Xaa is Glu(OtBu)
```

```
<220> FEATURE:
<221> NAME/KEY: MISC_FEATURE
<222> LOCATION: (16)..(16)
<223> OTHER INFORMATION: Xaa is Tyr(OtBu)
<220> FEATURE:
<221> NAME/KEY: MISC_FEATURE
<222> LOCATION: (22)..(22)
<223> OTHER INFORMATION: Xaa is Ser(Trt)
<220> FEATURE:
<221> NAME/KEY: MISC_FEATURE
<222> LOCATION: (23)..(23)
<223> OTHER INFORMATION: Xaa is Cys(Trt)
<220> FEATURE:
<221> NAME/KEY: MISC_FEATURE
<222> LOCATION: (24)..(24)
<223> OTHER INFORMATION: Xaa is homoarginine
<220> FEATURE:
<221> NAME/KEY: MISC_FEATURE
<222> LOCATION: (26)..(26)
<223> OTHER INFORMATION: Xaa is Asp(OtBu)
<220> FEATURE:
<221> NAME/KEY: MISC_FEATURE
<222> LOCATION: (29)..(29)
<223> OTHER INFORMATION: Xaa is Cys(Trt)

<400> SEQUENCE: 25

Phe Pro Xaa Pro Gly Gly Gly Gly Xaa Gly Xaa Ile Pro Xaa Xaa
1               5                   10                  15

Xaa Leu Gly Gly Gly Gly Xaa Xaa Xaa Gly Xaa Trp Pro Xaa
            20                  25

<210> SEQ ID NO 26
<211> LENGTH: 5
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
<223> OTHER INFORMATION: Xaa is a dipeptide consisting of any two acidic
      amino acids
<220> FEATURE:
<221> NAME/KEY: MISC_FEATURE
<222> LOCATION: (2)..(2)
<223> OTHER INFORMATION: Xaa is Val, Leu, Ile, Nle or Phe
<220> FEATURE:
<221> NAME/KEY: MISC_FEATURE
<222> LOCATION: (3)..(3)
<223> OTHER INFORMATION: Xaa is Hyp, Ser, Pro or an N-methyl amino acid
<220> FEATURE:
<221> NAME/KEY: MISC_FEATURE
<222> LOCATION: (4)..(4)
<223> OTHER INFORMATION: Xaa is a dipeptide consisting of any two acidic
      amino acids
<220> FEATURE:
<221> NAME/KEY: MISC_FEATURE
<222> LOCATION: (5)..(5)
<223> OTHER INFORMATION: Xaa is Tyr, Trp, Phe, Leu, Nle, Ile, Val, Cha
      or Pro

<400> SEQUENCE: 26

Xaa Xaa Xaa Xaa Xaa
1               5

<210> SEQ ID NO 27
<211> LENGTH: 7
<212> TYPE: PRT
<213> ORGANISM: artificial sequence
<220> FEATURE:
<223> OTHER INFORMATION: synthesized peptide
<220> FEATURE:
<221> NAME/KEY: MISC_FEATURE
<222> LOCATION: (1)..(1)
```

```
<223> OTHER INFORMATION: Xaa is Cys(Trt)
<220> FEATURE:
<221> NAME/KEY: MISC_FEATURE
<222> LOCATION: (2)..(2)
<223> OTHER INFORMATION: Xaa is homoarginine
<220> FEATURE:
<221> NAME/KEY: MISC_FEATURE
<222> LOCATION: (4)..(4)
<223> OTHER INFORMATION: Xaa is Asp(OtBu)
<220> FEATURE:
<221> NAME/KEY: MISC_FEATURE
<222> LOCATION: (7)..(7)
<223> OTHER INFORMATION: Xaa is Cys(Trt)

<400> SEQUENCE: 27

Xaa Xaa Gly Xaa Trp Pro Xaa
1               5
```